(12) United States Patent
Ikeuchi

(10) Patent No.: US 11,214,611 B2
(45) Date of Patent: *Jan. 4, 2022

(54) ANTIBODY CAPABLE OF BINDING TO INFLUENZA VIRUS INTRANUCLEAR PROTEIN, COMPLEX, DETECTION APPARATUS AND DETECTION METHOD USING SAME

(71) Applicant: Panasonic Intellectual Property Management Co., Ltd., Osaka (JP)

(72) Inventor: Emina Ikeuchi, Tokyo (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/726,981

(22) Filed: Dec. 26, 2019

(65) Prior Publication Data

US 2020/0165323 A1 May 28, 2020

Related U.S. Application Data

(63) Continuation of application No. PCT/JP2018/032306, filed on Aug. 31, 2018.

(30) Foreign Application Priority Data

Sep. 12, 2017 (JP) .............................. JP2017-174898
Jul. 12, 2018 (JP) .............................. JP2018-132404

(51) Int. Cl.
*C07K 16/10* (2006.01)
*G01N 33/569* (2006.01)
*C12Q 1/00* (2006.01)

(52) U.S. Cl.
CPC ... *C07K 16/1018* (2013.01); *G01N 33/56983* (2013.01); *C07K 2317/22* (2013.01); *C07K 2317/569* (2013.01); *C12Q 1/00* (2013.01); *G01N 2333/11* (2013.01)

(58) Field of Classification Search
None
See application file for complete search history.

(56) References Cited

U.S. PATENT DOCUMENTS

| 9,868,778 | B2 | 1/2018 | Muraoka |
| 10,287,325 | B2* | 5/2019 | Ikeuchi .............. C07K 16/1018 |
| 2013/0108638 | A1 | 5/2013 | Masat et al. |
| 2014/0302063 | A1 | 10/2014 | Hufton |
| 2017/0349646 | A1 | 12/2017 | Ikeuchi |
| 2017/0349647 | A1 | 12/2017 | Ikeuchi |

FOREIGN PATENT DOCUMENTS

| JP | 2014-159422 | 9/2014 |
| JP | 2014-527065 | 10/2014 |
| JP | 2017-036258 | 2/2017 |
| JP | 2018-058811 | 4/2018 |
| JP | 2018-058812 | 4/2018 |
| WO | 2007/074812 | 7/2007 |

OTHER PUBLICATIONS

International Search Report of PCT application No. PCT/JP2018/032306 dated Nov. 20, 2018.
Dan Zabetakis et al., "Contributions of the Complementarity Determining Regions to the Thermal Stability of a Single-Domain Antibody", PLOS ONE, vol. 8, Issue 10, e77678, Oct. 15, 2013.
Robert M. MacCallum et al., "Antibody-antigen Interactions: Contact Analysis and Binding Site Topography", J. Mol. Biol. (1996) 262, 732-745, Oct. 11, 1996.

* cited by examiner

*Primary Examiner* — Nicole Kinsey White
(74) *Attorney, Agent, or Firm* — McDermott Will & Emery LLP

(57) ABSTRACT

The present disclosure provides an antibody capable of binding to an intranuclear protein of an influenza virus and an application thereof. The present disclosure provides an antibody capable of recognizing a peptide consisting of the 205th-231st amino acid sequence in SEQ ID NO: 24.

14 Claims, 18 Drawing Sheets

Specification includes a Sequence Listing.

ANTIBODY CAPABLE OF BINDING TO INFLUENZA VIRUS INTRANUCLEAR PROTEIN, COMPLEX, DETECTION APPARATUS AND DETECTION METHOD USING SAME

CROSS-REFERENCE TO RELATED APPLICATION

This is a continuation of International Application No. PCT/JP2018/032306, with an international filing date of Aug. 31, 2018, which claims priority of Japanese Patent Application No. 2017-174898, filed on Sep. 12, 2017, and Japanese Patent Application No. 2018-132404, filed on Jul. 12, 2018, the contents of both of which are hereby incorporated by reference.

INCORPORATION BY REFERENCE SEQUENCE LISTING

The material contained in the ASCII text file named "P1017290US01-SL. txt" created on Dec. 26, 2019, and having a file size of 20,389 bytes is incorporated by reference herein.

TECHNICAL FIELD

The present disclosure relates to an antibody capable of binding to an intranuclear protein of an influenza virus, a complex, a detection apparatus and a detection method using the same.

BACKGROUND

Patent Literature 1 and Patent Literature 2 disclose an antibody capable of binding to an influenza virus. At least a part of the antibody disclosed in Patent Literature 1 and Patent Literature 2 is derived from alpaca. Patent Literature 1 and Patent Literature 2 are incorporated herein by reference.

CITATION LIST

Patent Literature 1: United States Patent Application Publication No. 2014/0302063
Patent Literature 2: Japanese Patent Application Publication No. 2017-036258

SUMMARY

One of the objects of the present disclosure is to provide a novel antibody capable of binging to the intranuclear protein of the influenza virus, a complex, a detection apparatus and a detection method using the same.

The present inventor has conducted intensive studies to achieve the object of the present disclosure, succeeded in obtaining a novel antibody, and succeeded in identifying an epitope.

The present disclosure relates to an isolated antibody which recognizes a peptide consisting of the 205th-231st amino acid sequence in SEQ ID NO: 24, a complex, a detection apparatus and a detection method using the same.

The present disclosure provides an isolated antibody which recognizes a peptide consisting of the 205th-231st amino acid sequence in SEQ ID NO: 24, a complex, a detection apparatus and a detection method using the same.

BRIEF DESCRIPTION OF THE DRAWINGS

Figure 4F:
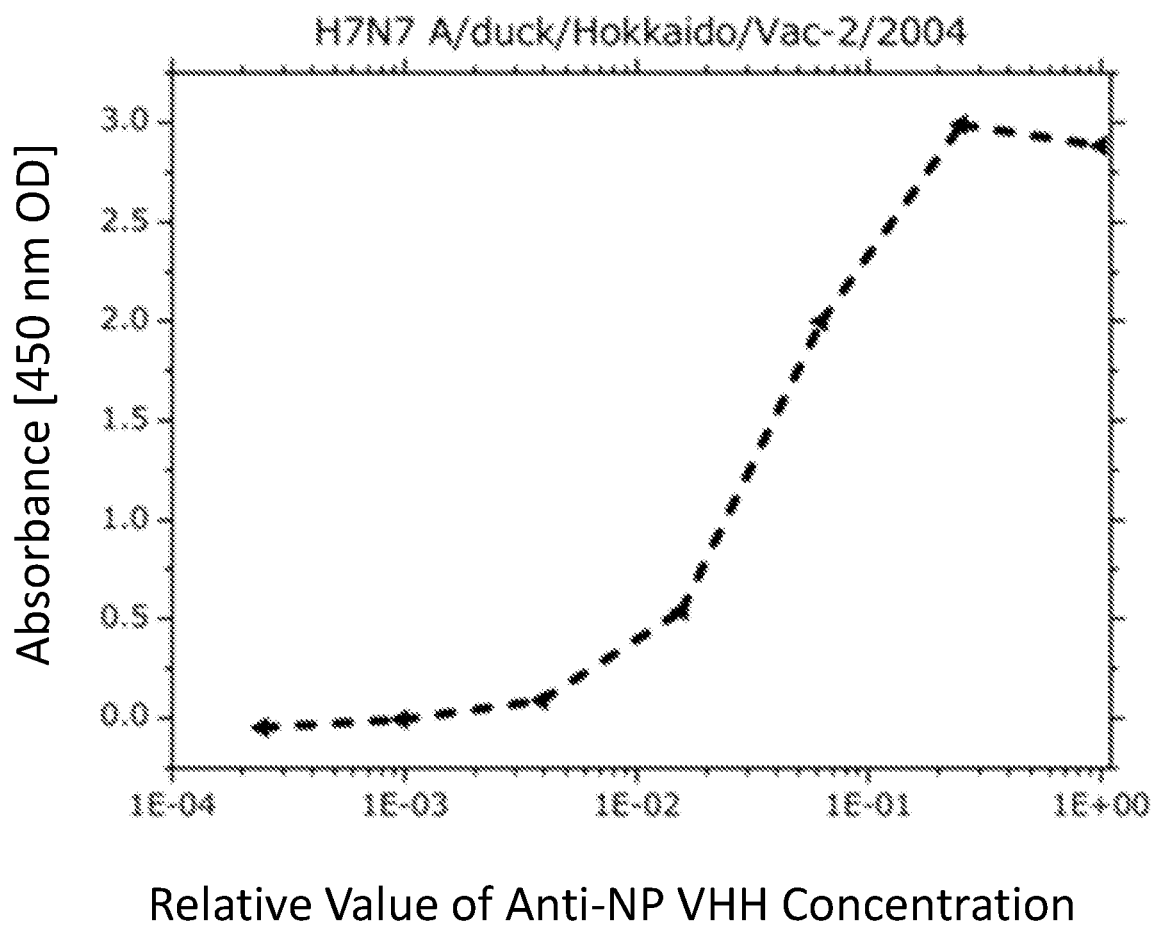
Figure 4H:
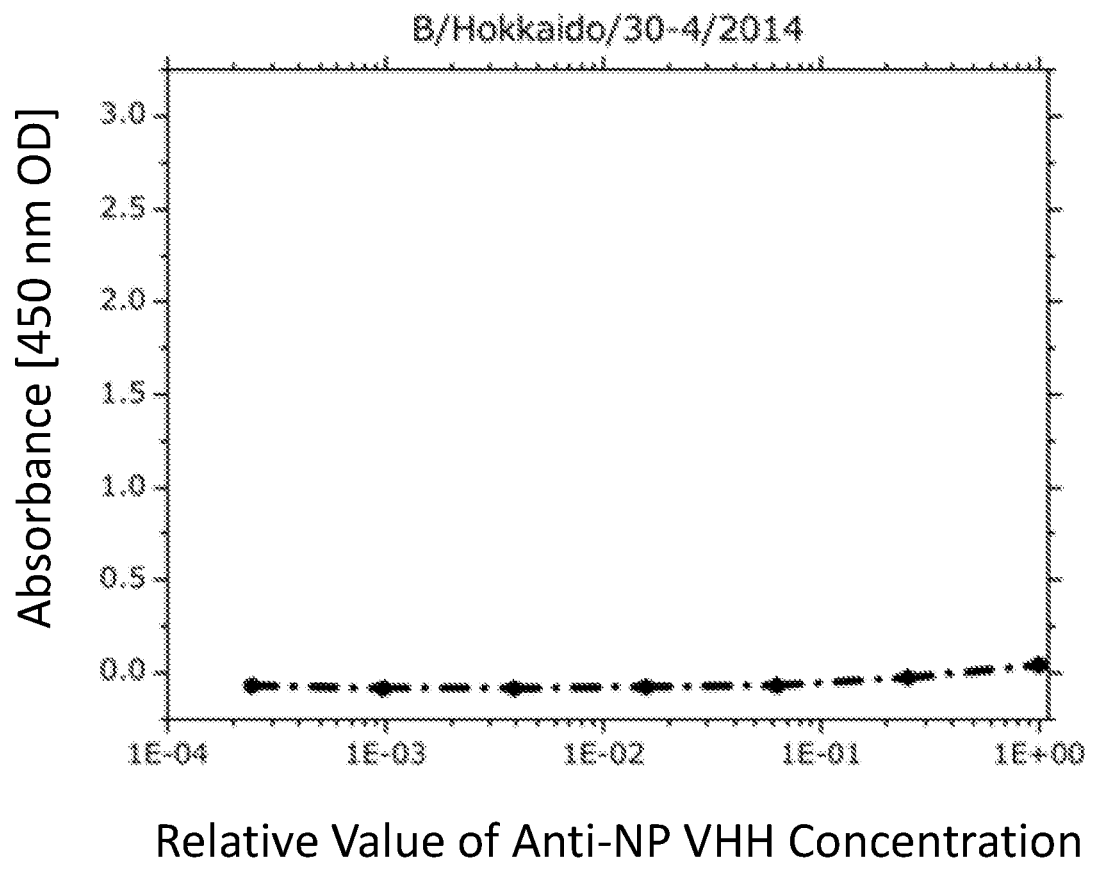

FIG. 4F is a graph showing the measurement results of the cross-reactivity of the VHH antibody containing the amino acid sequence represented by SEQ II) NO: 8 with regard to an influenza virus type A H7N7 A/duck/Hokkaido/Vac-2/2004.

FIG. 4H is a graph showing the measurement results of the cross-reactivity of the VH antibody containing the amino acid sequence represented by SEQ ID NO: 8 with regard to an influenza virus type B B/Hokkaido/30-4/2014.

DETAILED DESCRIPTION OF THE EMBODIMENT

Figure 1A:
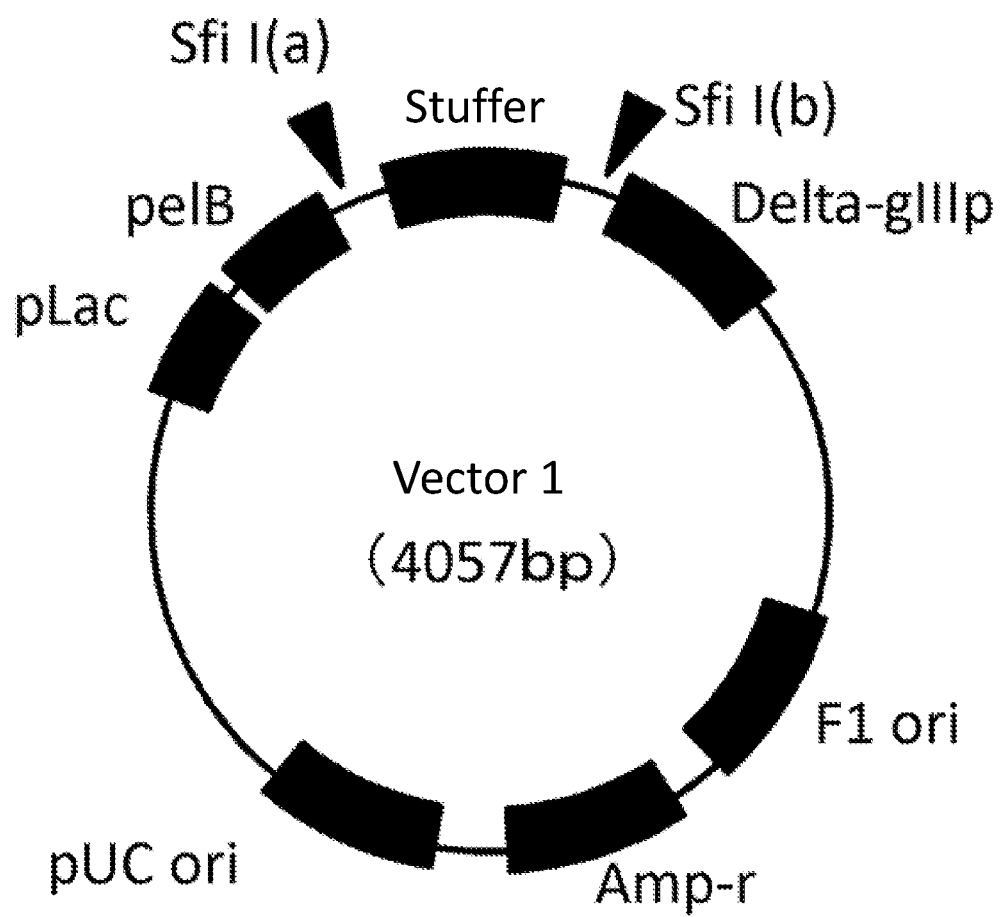
FIG. 1A shows a map of a vector used to ligate various genes contained in a gene library of a VHH antibody.

As used herein, the term "isolated antibody" does not include an antibody that is natural and has not been subjected to any external manipulation (artificial manipulation), namely, an antibody that has been produced in a body of an individual and remained there. Note that an isolated antibody typically exists in a state in which another type of an antibody is not mixed, namely, exists alone (as a group of antibodies of the same type).

In the present specification, "including" includes "consisting of" and "consisting essentially of".

In one aspect, the present disclosure relates to an isolated antibody capable of recognizing a peptide consisting of the 205th-231st amino acid sequence in SEQ ID NO: 24. More specifically, the present disclosure relates to an isolated antibody capable of recognizing an epitope contained in the peptide consisting of 205th-231st amino acid sequence in SEQ ID NO: 24.

In another aspect, the present disclosure relates to an isolated antibody capable of recognizing a peptide consisting of the 220th-231st amino acid sequence in SEQ ID NO: 24. More specifically, the present disclosure relates to an isolated antibody capable of recognizing an epitope contained in the peptide consisting of the 220th-231st amino acid sequence in SEQ ID NO: 24.

The antibody of the present disclosure recognizes a specific peptide in SEQ ID NO: 24. The present antibody is a polyclonal antibody or a monoclonal antibody, and is not limited to an antibody having the original complete structure as long as it has such a binding activity. For example, all the various derivatives derived from the complete antibody such as Fab, F (ab')2, or Fv fragment are included in the present antibody. In one embodiment, the antibody of the present disclosure is a VHH antibody.

In one embodiment, the antibody of the present disclosure can be isolated using techniques known to those skilled in the art by using a peptide consisting of the 205th-231st amino acid sequence in SEQ ID NO: 24.

In another embodiment, the antibody of the present disclosure can be isolated using techniques known to those skilled in the art by using a peptide consisting of the 220th-231st amino acid sequence in SEQ ID NO: 24.

The antibody of the present disclosure can be produced by any method known to those skilled in the art using the above-mentioned peptide or a complex of these and an appropriate adjuvant as an immunogen. For example, in the case where the antibody of the present disclosure is a polyclonal antibody, the antibody of the present disclosure can be obtained from serum after immunizing an animal with the above immunogen. Alternatively, the antibody of the present disclosure can be prepared by introducing an expression vector coding for the above-mentioned immunogen into the muscle or skin of an animal by injection or with a gene gun, and then collecting the serum. Examples of the animals that can be used include mice, rats, rabbits, goats, chickens, camels, and alpaca. Monoclonal antibodies can also be prepared by a method in which antibodies are produced by continuous cell culture. Examples of the method are a hybridoma method (Nature, 1975, Vol. 256, p. 495-497), a trioma method, a human B cell hybridoma method (Immunology Today, 1983, Vol. 4, p. 72), and the EBV-hybridoma method (Monoclonal Antibodies and Cancer Therapy, 1985, pp. 77-96, Alan R. Liss, Inc.).

Whether or not the produced antibody binds to the target peptide can be measured by a known means (Antibodies A Laboratory Manual. Ed Harlow, David Lane, Cold Spring Harbor Laboratory, 1988). For example, ELISA (enzyme-linked immunosorbent assay), EIA (enzyme immunoassay), RIA (radioimmunoassay) or fluorescent immunoassay can be used.

The antibody according to the present disclosure binds to a type-A influenza virus. In particular, the antibody according to the present disclosure binds to an intranuclear protein of the type-A influenza virus. As disclosed in Patent Literature 1, an antibody capable of binding to the influenza virus includes an amino acid sequence containing the following structural domain in the N to C direction: N-FR1-CDR1-FR2-CDR2-FR3-CDR3-FR4-C, where FR indicates an amino acid sequence of a framework region, and CDR indicates an amino acid sequence of a complementarity determining region.

In the present disclosure, for example, CDR1 includes the amino acid sequence represented by GSAFSLYAMG (SEQ ID NO: 1).

In the present disclosure, CDR2 includes the amino acid sequence represented by, for example, YITNGDITNY-ADSVQG (SEQ ID NO: 2).

In the present disclosure, CDR3 includes the amino acid sequence represented by, for example, VGGRTF (SEQ ID NO: 3).

Desirably, CDR1, CDR2, and CDR3 are represented by, for example, SEQ ID NO: 1, SEQ ID NO: 2, and SEQ ID NO: 3, respectively. In this case, more desirably, FR1, FR2, FR3, and FR4 includes amino acid sequences represented by QLQLVESGGGLVQAGGSLRLSCAAS (SEQ ID NO: 4), WHRQAPGKQRELVA (SEQ ID NO: 5), RVIISRD-NAKNTVYLHMNSLKPEDTAVYYCYA (SEQ ID NO: 6), and WGQGTQVTVSS (SEQ ID NO: 7), respectively.

In other words, the antibody according to the present disclosure can include the following amino acid sequence: QLQLVESGGGLVQAGGSLRLSCAASGSAFS-LYAMGWHRQAPGKQRELVAYITNGDITNY-ADSVQGRVIISRDNAKNT VYLHMNSLKPED-TAVYYCYAVGGRTFWGQGTQVTVSS (SEQ ID NO: 8).

An antibody containing the amino acid sequence represented by SEQ ID NO: 8 does not exhibit an antigen cross-reactivity with an influenza virus other than type-A influenza virus, for example, with an influenza virus such as type-B influenza virus. The antibody of the present disclosure may be lyophilized or mixed with a known stabilizer in order to stably store for a long period of time.

The antibody of the present disclosure can be used in a detection apparatus or a detection method for detecting an intranuclear protein of the type-A influenza virus. In this case, the antibody of the present disclosure may be used in a state of a complex bound to another substance, for example, a complex bound to at least one of a carrier and a labeling substance.

The shape and material of the carrier are not particularly limited, as long as it is a carrier insoluble in a solvent in a reaction system of an antigen-antibody reaction. Examples of the shape of the carrier include a plate, a bead, a disk, a tube, a filter, and a thin film. Examples of the material of the carrier include a polymer such as polyethylene terephthalate, cellulose acetate, polycarbonate, polystyrene, or polymethyl methacrylate, a metal such as gold, silver, or aluminum, and glass. As a method for binding the antibody to the carrier, a known method such as a physical adsorption method, a covalent bond method, an ionic bond method, or a cross-linking method is used.

As the labeling substance, for example, a fluorescent substance, a luminescent substance, a dye, an enzyme, or a radioactive substance is used. As a method for binding the antibody to the labeling substance, a known method such as a physical adsorption method, a covalent bond method, an ionic bond method, or a crosslinking method is used.

In the detection method using the antibody of the present disclosure, a complex containing the antibody and an analyte are brought into contact, and a change in physical quantity based on the antigen-antibody reaction of the intranuclear protein of the type-A influenza virus in the analyte and the antibody of the complex is detected. Examples of the physical quantity include emission intensity, chromaticity, light transmittance, turbidity, absorbance, and radiation dose. Specific examples of the detection method include known methods such as enzyme immunoassay, immunochromatography, latex agglutination, radioimmunoassay, fluorescence immunoassay, and surface plasmon resonance measurement.

The detection apparatus using the antibody of the present disclosure includes a detection part for detecting any of the physical quantities that change based on the antigen-antibody reaction. The detection part is composed of well-known apparatuses such as various photometers, spectrometers, and dosimeters.

The antibody of the present disclosure can be used not only as the complex bound to another substance but also as a composition containing the antibody of the present disclosure or a kit including the antibody of the present disclosure.

The present disclosure further provides the followings. (1): an isolated antibody capable of recognizing the peptide consisting of the 205th-231st amino acid sequence in SEQ ID NO: 24; (2): an isolated antibody capable of recognizing an epitope contained in the peptide consisting of the 220th-231st amino acid sequence in SEQ ID NO: 24; (3) an antibody according to (1) or (2), wherein the antibody is a VHH antibody; (4) a complex including any one of (1)-(3), wherein the antibody has been bound to at least one of a carrier and a labeling substance; (5): the complex according to (4), wherein the carrier is selected from a plate, a bead, a disk, a tube, a filter, and a thin film; (6) the complex according to (4), wherein the labeling substance is selected from a fluorescent substance, a luminescent substance, a dye, an enzyme and a radioactive substance; (7): a detection device including the complex according to (4) and a detection part, wherein the detection part detects a change in physical quantity based on an antigen-antibody reaction between the intranuclear protein in an analyte and the complex; and (8): a detection method including a step of bringing the complex according to (4) into contact with an analyte, and a step of detecting a change in physical quantity based on an antigen-antibody reaction between the intranuclear protein in the analyte and the complex.

EXAMPLES

Inventive Example 1

VHH antibodies (i.e., a variable domain of a heavy chain of a heavy chain antibody) were prepared in accordance with the following procedures as a peptide capable of binding to an intranuclear protein included in a type-A influenza virus H1N1. Hereinafter, the intranuclear protein is referred to as "NP".

(Immunization of Alpaca and Acquirement of Mononuclear) In order to form a VHH antibody gene library, an alpaca was immunized using a recombinant intranuclear protein (SEQ ID NO: 24) derived from a type-A influenza virus H1N1 (A/Puerto Rico/8/34/Mount Sinai) as an antigen. The recombinant intranuclear protein was prepared using a Brevibacillus expression system by Higeta Shoyu Co., Ltd. The recombinant intranuclear protein was prepared with an adjuvant before administrated to an alpaca.

The recombinant intranuclear protein (SEQ ID NO: 24) used in the inventive example 1 is shown below.

(SEQ ID NO: 24)
MASQGTKRSYEQMETDGERQNATEIRASVGKMIGGIGRFYIQMCTELKLS

DYEGRLIQNSLTIERMVLSAFDERRNKYLEEHPSAGKDPKKTGGPIYRRV

NGKWMRELILYDKEEIRRIWRQANNGDDATAGLTHMMIWHSNLNDATYQR

TRALVRTGMDPRMCSLMQGSTLPRRSGAAGAAVKGVGTMVMELVRMIKRG

INDRNFWRGENGRKTRIAYERMCNILKGKFQTAAQKAMMDQVRESRNPGN

AEFEDLTFLARSALILRGSVAHKSCLPACVYGPAVASGYDFEREGYSLVG

IDPFRLLQNSQVYSLIRPNENPAHKSQLVWMACHSAAFEDLRVLSFIKGT

KVLPRGKLSTRGVQIASNENMETMESSTLELRSRYWAIRTRSGGNTNQQR

ASAGQISIQPTFSVQRNLPFDRTTIMAAFNGNTEGRTSDMRTEIIRMMES

ARPEDVSFQGRGVFELSDEKAASPIVPSFDMSNEGSYFFGDNAEEYDN

Specifically, the recombinant intranuclear protein having a concentration of 100 micrograms/milliliter was administered to the alpaca. After one week, the recombinant intranuclear protein having the same concentration was administered to the alpaca, again. In this way, the alpaca was immunized with the recombinant intranuclear protein five times for five weeks. After another week, blood of the alpaca was extracted. Then, mononuclear cells were acquired from the blood as below.

A blood cell separation solution (available from COSMO BIO Co., Ltd., trade name: Lymphoprep) was added to a lymphocyte separation tube (available from Greiner Bio-One Co., Ltd., trade name: Leucosep). Then, the solution was subjected to centrifugation at a temperature of 20 degrees Celsius at 1,000×g for one minute.

The blood extracted from the alpaca was treated with heparin. Then, an equivalent amount of phosphate buffered saline (hereinafter, referred to as "PBS") was added to the thus-treated blood to obtain a sample solution. Then, the sample solution was added to the lymphocyte separation tube containing the blood cell separation solution.

The lymphocyte separation tube was subjected to centrifugation at a temperature of 20 degrees Celsius at 800×g for thirty minutes.

A fraction containing the mononuclear cells was collected. PBS three times in volume was added. The fraction was subjected to centrifugation at a temperature of 20 degrees Celsius at 300×g for five minutes. The precipitate was suspended with PBS gently. After the suspending, 10 microliters of the suspension was separated in order for the count of the number of cells. The remaining suspension was subjected to centrifugation at a temperature of 20 degrees Celsius at 300×g for five minutes.

An RNA storage solution (trade name: RNAlater) having a volume of 2 milliliters was added to the precipitate. Then, the solution was suspended gently. The suspension was injected into two tubes each having a volume of 1.5 milliliters. Each tube included 1 milliliter of the suspension. The tube was stored at a temperature of −20 degrees Celsius. The suspension (5 microliters) separated for the count of the number of cells was mixed with a Turk's solution (15 microliters), and the number of the mononuclear cells was counted with a counting chamber.

(Formation of cDNA Gene Library of VHH Antibody)

Then, a total RNA was extracted from the mononuclear cells, and a cDNA gene library of the VHH antibody was formed in accordance with the following procedure. In the following procedure, RNase-free-grade reagents and instruments were used.

A total RNA isolation reagent (trade name: TRIzol Reagent, 1 milliliter) was added to the mononuclear cell fraction. The reagent was mixed gently and left at room temperature for five minutes. Chloroform (200 microliters) was added to the reagent, and the reagent was shaken strongly for fifteen seconds. The reagent was left at rest at room temperature for two-three minutes. The reagent was subjected to centrifugation at not more than 12,000×g at a temperature of 4 degrees Celsius for 15 minutes.

The supernatant was moved to a new tube. RNase-free water and chloroform (200 microliters, each) were added to the tube. In addition, 500 milliliters of isopropanol was added to the tube. The liquid contained in the tube was stirred with a vortex mixer. The liquid was left at rest at room temperature for ten minutes. Then, the liquid was subjected to centrifugation at not more than 12,000×g at a temperature of 4 degrees Celsius for fifteen minutes. The supernatant was removed, and the precipitate was rinsed with one milliliter of 75% ethanol. This solution was subjected to centrifugation at not more than 7,500×g at a temperature of four degrees Celsius for five minutes. The solution was dried to obtain total RNA. The obtained total RNA was dissolved in RNase-free water.

In order to obtain cDNA from the total RNA, a kit including a reverse transcriptase was employed. The kit was available from Takara Bio Inc., as a trade name of PrimeScript II 1$^{st}$ strand cDNA Synthesis Kit. The Random 6 mer and Oligo dT primer included in the kit were used as primers. The cDNA was obtained in accordance with the standard protocol attached to the kit.

The gene of the VHH antibody included in the alpaca was obtained from the cDNA by a PCR method. An enzyme for PCR was available from Takara Bio Inc., as a trade name of Ex-taq.

The following reagents were mixed to obtain a mixture solution.

| | |
|---|---|
| 10 × buffer | 5 microliters |
| dNTPs | 4 microliters |
| Primer F | 2 microliters |
| Primer R | 2 microliters |
| cDNA template | 1 microliter |
| Ex-taq | 0.25 microliters |

The mixture solution was subjected to the following PCR method.

First, the mixture solution was heated at a temperature of 95 degrees Celsius for two minutes. Then, the temperature of the mixture solution was varied in accordance with the following cycle:

Ninety six degrees Celsius for thirty seconds:
Fifty two degrees Celsius for thirty seconds; and
Sixty eight degrees Celsius for forty seconds.
This cycle was repeated thirty times.

Finally, the mixture solution was heated at a temperature of sixty eight degrees Celsius for four minutes and stored at a temperature of four degrees Celsius.

The following primers were used in the present PCR method.

Primer 1:
(SEQ ID NO: 9)
5'-GGTGGTCCTGGCTGC-3'

Primer 2:
(SEQ ID NO: 10)
5'-ctgctcctcgcGGCCCAGCCGGCCatggcTSAGKTGCAGCTCGTGG

AGTC-3'

Primer 3:
(SEQ ID NO: 11)
5'-TGGGGTCTTCGCTGTGGTGCG-3'

Primer 4:
(SEQ ID NO: 12)
5'-TTGTGGTTTTGGTGTCTTGGG-3'

Primer 5:
(SEQ ID NO: 13)
5'-tttgCtctGCGGCCGCagaGGCCgTGGGGTCTTCGCTGTGGTG

CG-3'

Primer 6:
(SEQ ID NO: 14)
5'-tttgCtctGCGGCCGCagaGGCCgaTTGTGGTTTTGGTGTCTTG

GG-3'

(Reference Literature: Biomed Environ Sci., 2012; 27(2): 118-121)

Three PCR assays were conducted.

In the first PCR assay, a primer set A composed of the cDNA, Primer 1 and Primer 3 and a primer set B composed of the cDNA, Primer 1 and Primer 4 were used.

In the second PCR assay, a primer set C composed of the gene amplified with the primer set A, Primer 2, and Primer 3, and a primer set 1) composed of the gene amplified with the primer set B, Primer 2, and Primer 4 were used.

In the third PCR assay, a primer set E composed of the gene amplified with the primer set C, Primer 2, and Primer 5, and a primer set F composed of the gene amplified with the primer set D, Primer 2, and Primer 6 were used. In this way, the gene library of the VHH antibody was formed. In other words, the gene library of the VHH antibody included the genes amplified with the primer sets E and F.

(Formation of Phage Library)

Next, a phage library was formed from the gene library of the VHH antibody in accordance with the following procedures.

Figure 1B:
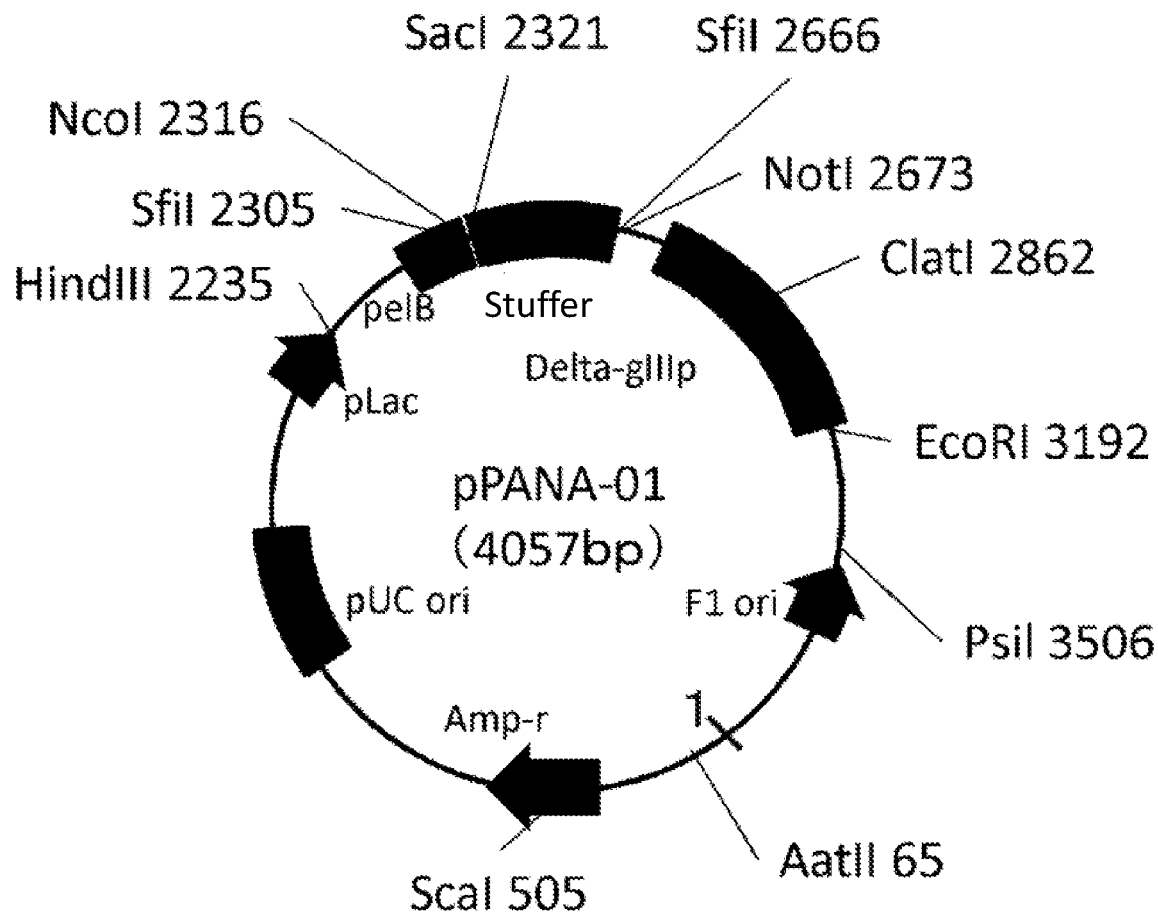
FIG. 1B shows details of the vector map shown in FIG. 1A.

A plasmid Vector 1 (4057 bp, see FIG. 1A) derived from a commercially available plasmid pUC119 (for example, available from Takara Bio Inc.) was treated with a restriction enzyme SfiI. The restriction enzyme site SfiI (a) shown in FIG. 1A consists of the gene sequence represented by GGCCCAGCCGGCC (SEQ II) NO: 15). The restriction enzyme site SfiI (b) consists of the gene sequence represented by GGCCTCTGCGGCC (SEQ ID NO: 16). FIG. 1B shows a detailed vector map of the plasmid Vector 1.

The plasmid Vector 1 consists of the following gene sequence.

(SEQ ID NO: 17)
```
gacgaaagggcctcgtgatacgcctattttataggttaatgtcatgata
ataatggtttcttagacgtcaggtggcacttttcggggaaatgtgcgcgg
aaccccta tttgtttattttt ctaaatacattcaaatatgtatccgctca
tgagacaataaccctgataaatgcttcaataatattgaaaaaggaagagt
atgagtattcaacatttccgtgtcgcccttattccttttttgcggcatt
ttgccttcctgttttt gctcacccagaaacgctggtgaaagtaaaagatg
ctgaagatcagttgggtgcacgagtgggttacatcgaactggatctcaac
agcggtaagatccttgagagttttcgccccgaagaacgttttccaatgat
gagcacttttaaagttctgctatgtggcgcggtattatcccgtattgacg
ccgggcaagagcaactcggtcgccgcatacactattctcagaatgacttg
gttgagtactcaccagtcacagaaaagcatcttacggatggcatgacagt
aagagaattatgcagtgctgccataaccatgagtgataacactgcggcca
acttacttctgacaacgatcggaggaccgaaggagctaaccgcttttttg
cacaacatgggggatcatgtaactcgccttgatcgttgggaaccggagct
gaatgaagccataccaaacgacgagcgtgacaccacgatgcctgtagcaa
tggcaacaacgttgcgcaaactattaactggcgaactacttactctagct
tcccggcaacaattaatagactggatggaggcggataaagttgcaggacc
acttctgcgctcggcccttccggctggctggtttattgctgataaatctg
gagccggtgagcgtgggtctcgcggtatcattgcagcactggggccagat
ggtaagccctcccgtatcgtagttatctacacgacggggagtcaggcaac
tatggatgaacgaaatagacagatcgctgagataggtgcctcactgatta
agcattggtaactgtcagaccaagtttactcatatatactttagattgat
ttaaaacttcattttta atttaaaaggatctaggtgaagatcctttttga
taatctcatgaccaaaatcccttaacgtgagttttcgttccactgagcgt
cagaccccgtagaaaagatcaaaggatcttcttgagatcctttttttctg
cgcgtaatctgctgcttgcaaacaaaaaaaccaccgctaccagcggtggt
ttgtttgccggatcaagagctaccaactctttttccgaaggtaactggct
tcagcagagcgcagataccaaatactgtccttctagtgtagccgtagtta
ggccaccacttcaagaactctgtagcaccgcctacatacctcgctctgct
aatcctgttaccagtggctgctgccagtggcgataagtcgtgtcttaccg
ggttggactcaagacgatagttaccggataaggcgcagcggtcgggctga
acggggggttcgtgcacacagcccagcttggagcgaacgacctacaccga
actgagatacctacagcgtgagctatgagaaagcgccacgcttcccgaag
ggagaaaggcggacaggtatccggtaagcggcagggtcggaacaggagag
cgcacgagggagcttccaggggaaacgcctggtatctttatagtcctgt
cgggtttcgccacctctgacttgagcgtcgatttttgtgatgctcgtcag
ggggg cggagcctatgga aaaacgccagcaacgcggcctttttacggttc
ctggccttttgctggccttttgctcacatgttctttcctgcgttatccc
tgattctgtggataaccgtattaccgcctttgagtgagctgataccgctc
gccgcagccgaacgaccgagcgcagcgagtcagtgagcgaggaagcggaa
```
-continued
```
gagcgcccaatacgcaaaccgcctctccccgcgcgttggccgattcatta
atgcagctggcacgacaggtttcccgactggaaagcgggcagtgagcgca
acgcaattaatgtgagttagctcactcattaggcaccccaggctttacac
tttatgcttccggctcgtatgttgtgtggaattgtgagcggataacaatt
tcacacaggaaacagctatgaccatgattacgccAAGCTTCGAAGGAGAC
AGTCATAatgaaatacctgctgccgaccgctgctgctggtctgctgctcc
tcgcGGCCCAGCCGGCCatggagcTCAAGATGACACAGACTACATCCTCC
CTGTCAGCCTCTCTGGGAGACAGAGTCACCATCAGTTGCAGGGCAAGTCA
GGACATTAGCGATTATTTAAACTGGTATCAGCAGAAACCAGATGGAACTG
TTAAACTCCTGATCTATTACACATCAAGTTTACACTCAGGAGTCCCATCA
AGGTTCAGTGGCGGTGGGTCTGGAACAGATTATTCTCTCACCATTAGCAA
CCTGGAGCAAGAAGATATTGCCACTTACTTTTGCCAACAGGGTAATACGC
TTCCGTGGACGTTTGGTGGAGGCACCAAGCTGGAAATCAAACGGGCTGAT
GCTGCACCAACTGtaGGCCtctGCGGCCGCagaGcaaaaactcatctcag
aagaggatctgaatggggccgcaTAGggttccggtgattttgattatgaa
aagatggcaaacgctaataaggggg ctatgaccgaaaatgccgatgaaaa
cgcgctacagtctgacgctaaaggcaaacttgattctgtcgctactgatt
acggtgctgctatcgatggtttcattggtgacgtttccggccttgctaat
ggtaatggtgctactggtgattttgctggctctaattcccaaatggctca
agtcggtgacggtgataattcaccttta atgaataatttccgtcaatatt
taccttccctccctcaatcggttgaatgtcgcccttttgtctttagcgct
ggtaaaccatatgaattttctattgattgtgacaaaataaacttattccg
tggtgtctttgcgtttcttttatatgttgccacctttatgtatgtatttt
ctacgtttgctaacatactgcgtaataaggagtctTAATAAgaattcact
ggccgtcgttttacaacgtcgtgactgggaaaaccctggcgttacccaac
ttaatcgccttgcagcacatccccctttcgccagctggcgtaatagcgaa
gaggcccgcaccgatcgcccttcccaacagttgcgcagcctgaatggcga
atggcgcctgatgcggtattttctccttacgcatctgtgcggtatttcac
accgCATATGaAAATTGTAAgcgttaatattttgttaaaattcgcgttaa
atttttgttaaatcagctcattttttaaccaataggccgaaatcggcaaa
atcccttataaatcaaaagaatagaccgagatagggttgagtgttgttcc
agtttggaacaagagtccactattaaagaacgtggactccaacgtcaaag
ggcgaaaaccgtctatcagggcgatggcccactacgtgaaccatcaccc
taatcaagttttttggggtcgaggtgccgtaaagcactaaatcggaaccc
taaaggagccccctagagcttgacggggaaagccggcgaacgtgg
cgagaaaggaagggaagaaagcgaaaggagcgggcgctagggcgctggca
agtgtagcggtcacgctgcgcgtaaccaccacacccgccgcgcttaatgc
gccgctacaGGGCGCGTcccatATGgtgcactctcagtacaatctgctct
gatgccgcatagttaagccagccccgacacccgccaacacccgctgacgc
```

-continued gccctgacgggcttgtctgctcccggcatccgcttacagacaagctgtga ccgtctccgggagctgcatgtgtcagaggttttcaccgtcatcaccgaaa cgcgcga Similarly, the gene library of the VHH antibody was treated with the restriction enzyme SfiI. In this way, VHH antibody gene fragments were obtained.

The thus-treated plasmid Vector 1 was mixed with the VHH antibody gene fragments at a ratio of 1:2. An enzyme (available from Toyobo Co. Ltd., trade name: Ligation High ver. 2) was injected into the mixture solution. The mixture solution was left at rest at a temperature of 16 degrees Celsius for two hours. In this way, each of the VHH antibody gene fragments was ligated into the plasmid Vector 1.

Coli bacteria (available from Takara Bio Inc., trade name: HST02) were transfected with the thus-ligated plasmid Vector 1.

Then, the coli bacteria were incubated for fifteen hours on a 2YT plate culture medium containing ampicillin at a concentration of 100 micrograms/milliliter. In this way, obtained was a library of phages each of which displays a protein obtained from the gene fragment included in the gene library of the VHH antibody.

After the incubation, a concentration of the library was calculated by counting the number of single colonies formed on the 2YT plate culture medium. As a result, the library of the phages had a concentration of $5 \times 10^2$/milliliter.

(Biopanning)

VHH antibodies specifically binding to the intranuclear protein were obtained from the phage library in accordance with the following procedures.

In order to extract the clones each capable of binding to the antigen from among the phages which expressed the VHH antibody, biopanning was conducted twice.

Coli bacteria (HST02) into which the VHH antibody gene fragment included in the gene library of the VHH antibody was introduced were incubated at a temperature of 30 degrees Celsius in the 2YT AG culture medium containing 100 micrograms/milliliter of ampicillin and 1% glucose, until a value OD, indicating absorbance reached 1.0. The 2YT AG culture medium has a volume of 100 milliliters. In this way, the coli bacteria were proliferated.

Helper phages (available from Invitrogen company, trade name: M13K07) were added to the coli bacteria culture medium in such a manner that the multiplicity of infection (MOI) was approximately 20.

Then, the culture medium was warmed at a temperature of 37 degrees Celsius for about thirty minutes. Then, the culture medium was subjected to centrifugation at a rotation speed of 4,000 rpm for ten minutes to collect the coli bacteria. The coli bacteria were incubated overnight at a temperature of 30 degrees Celsius in a 2YTAK culture medium (i.e., a 2YT culture containing 100 micrograms/milliliter of ampicillin and 50 micrograms/milliliter of kanamycin), while subjected to centrifugation at 213 rpm. The 2YTAK culture medium has a volume of 100 milliliters.

The incubation liquid (100 milliliters) containing the thus-incubated coli bacteria was injected into two centrifugation tubes (volume: 50 milliliters, each). The two centrifugation tubes were subjected to centrifugation at a rotation speed of 4,000 rpm for ten minutes. Then, the supernatants (20 milliliters, each) were collected.

The supernatants (40 milliliters) were added to a 20% polyethylene glycol solution (10 milliliters) containing NaCl (2.5 M). Then, the mixture solution was mixed upside down. Subsequently, the mixture solution was cooled on ice for approximately one hour. The mixture solution was subjected to centrifugation at a rotation speed of 4,000 rpm for ten minutes. Then, the supernatant was removed. PBS containing 10% glycerol was injected toward the precipitate. Finally, the precipitate was loosened and dissolved. In this way, a library of phages each of which displays the VHH antibody was obtained.

(Screening of VHH Antibody Capable of Specifically Binding to NP)

(A) Immobilization of NP Antigen

NP was mixed with PBS to prepare an NP solution. The concentration of NP was 2 micrograms/milliliter. The NP solution (2 milliliters) was injected into an immunotube (available from NUNC Co., Ltd.). The NP solution was left at rest in the immunotube overnight. In this way, NP was immobilized in the immunotube. Then, the inside of the immunotube was washed three times with PBS. The inside of the immunotube was filled with PBS which contained 3% skim milk (available from Wako Pure Chemical Industries, Ltd.). In this way, NP was blocked as an antigen in the immunotube. The immunotube was left at rest at room temperature for one hour. Subsequently, the inside of the immunotube was washed three times with PBS.

(B) Panning

The library of the phages each of which displays the VHH antibody (concentration: approximately 5E+11/milliliter) was mixed with 3 milliliters of PBS containing 3% skim milk to prepare a mixture solution. The mixture solution was injected into the immunotube in which the NP antigen was immobilized. A lid formed of a parafilm was attached to the immunotube. Then, the immunotube was rotated upside down in a rotator for ten minutes. The immunotube was left at rest at room temperature for one hour. The inside of the immunotube was washed ten times with PBS containing 0.05% Tween 20. Hereinafter, such PBS is referred to as "PBST". The inside of the immunotube was filled with PBST. Subsequently, the immunotube was left at rest for ten minutes. Then, the inside of the immunotube was washed ten times with PBST.

In order to extract phages each of which displays the VHH antibody bound to the NP antigen, a 100 mM trimethylamine solution (1 milliliter) was injected into the immunotube. A lid formed of a parafilm was attached to the immunotube. Then, the immunotube was rotated upside down in a rotator for ten minutes.

In order to neutralize the solution, the solution was moved to a tube containing 1 mL of 0.5 M Tris/HCl (pH: 6.8). Again, the extraction of the phage was repeated using a 100 mM trimethylamine solution (1 milliliter). In this way, 3 mL of an extraction liquid was obtained.

The extraction liquid (1 mL) was mixed with 9 mL of coli bacteria HST02. The mixture solution was left at rest for one hour at a temperature of 30 degrees Celsius.

In order to count the number of colonies, 10 microliters of the mixture solution containing the coli bacteria HST02 was distributed onto a small plate including a 2TYA culture medium (10 milliliters/plate).

The rest of the mixture solution was subjected to centrifugation. The supernatant was removed, and the precipitate was distributed onto a large plate including a 2TYA culture medium (40 milliliters/plate). These two plates were left at rest overnight at a temperature of 30 degrees Celsius. In this way, first panning was conducted.

Second panning was conducted identically to the procedure of the first panning. In other words, the panning was repeated. In this way, the monoclonal phages on which the VHH antibody was displayed were purified.

After the second panning, a colony of the coli bacteria was picked up with a toothpick. The picked-up colony was put on one well of 96-flat-bottom plate. This was repeated. One well contained 200 microliters of a 2YTAG culture medium.

The solutions included in the wells were stirred at a rotation speed of 213 rpm at a temperature of 30 degrees Celsius.

The solution (50 microliters) containing grown coli bacteria was collected. The collected solution was mixed with 50 microliters of a 2YTA culture medium included in a plate. The 2YTA culture medium contained helper phages such that the multiplicity of infection was set to be 20. The solution was left at rest at a temperature of 37 degrees Celsius for forty minutes.

The plate including the 2YTA culture medium was subjected to centrifugation at 1,800 rpm for twenty minutes. The supernatant was removed. The precipitate contained the coli bacteria. The precipitate was mixed with 200 microliters of a 2YTAK culture medium. The mixture solution was left at rest overnight at a temperature of 30 degrees Celsius.

The mixture solution was subjected to centrifugation at 1,800 rpm for twenty minutes. The supernatant containing the coli bacteria was collected.

(C) Qualitative Evaluation of Phage-Displayed VHH Antibody and Antigen by ELISA

An intranuclear protein solution having a concentration of 2 micrograms/milliliter was injected as an antigen into each of the wells of a 96-well plate (available from Thermo scientific company, trade name: maxisorp). The volume of the intranuclear protein solution in each well was 50 microliters. The 96-well plate was left overnight at a temperature of 4 degrees Celsius. In this way, the NP antigen was immobilized in each well.

Each of the wells was washed three times with PBS. Then, PBS containing 3% skim milk (available from Wako Pure Chemical Industries, Ltd.) was injected into each well (200 microliters/well). The 96-well plate was left at room temperature for one hour. In this way, the intranuclear protein was blocked in each well. Subsequently, each well was washed three times with PBS.

The monoclonal phages each of which displays the VHH antibody were injected into each well (50 microliters/well). Then, the 96-well plate was left at rest for one hour. In this way, the phages reacted with the NP antigen.

Each well was washed three times with PBST. Then, an anti-M13 antibody (available from ABCAM company, trade name; ab50370, 10,000-fold dilution) was injected into each well (50 microliters/well). Then, each well was washed three times with PBST.

A color-producing agent (available from Thermo Scientific, trade name: 1-step ultra TMB-ELISA) was injected into each well (50 microliters/well). The 96-well plate was left at rest for two minutes to cause the color-producing agent to react with the antibody.

A sulfuric acid aqueous solution (normal, i.e., 1 N) was injected into each well at a concentration of 50 microliters/well to cease the reaction.

The absorbance of the solution at a wavelength of 450 nanometers was measured.

Fourteen wells each having good absorbance measurement result were selected. The DNA sequences included in the phages contained in the selected fourteen wells were analyzed by Greiner Company. The analysis results of the DNA sequences will be described below. The following one DNA sequence was found.

```
                                        (SEQ ID NO: 18)
CAGTTGCAGCTCGTGGAGTCTGGGGGAGGCTTGGTGCAGGCTGGGGGGTC

TCTGAGACTCTCCTGTGCAGCCTCTGGAAGCGCCTTCAGCCTCTATGCCA

TGGGCTGGCACCGCCAGGCTCCAGGGAAGCAGCGCGAGTTGGTCGCATAT

ATTACTAATGGTGACATCACAAACTATGCGGACTCCGTGCAGGGCCGTGT

CATCATCTCCAGAGACAACGCCAAAAACACGGTGTATCTACACATGAACA

GCCTGAAACCTGAGGACACAGCCGTCTATTATTGTTATGCAGTGGGGGGT

CGGACCTTCTGGGGCCAGGGGACCCAGGTCACCGTCTCCTCA
```

The protein synthesized from the DNA sequence represented by SEQ ID NO: 18 consists of the following amino acid sequence.

```
                                         (SEQ ID NO: 8)
QLQLVESGGGLVQAGGSLRLSCAASGSAFSLYAMGWHRQAPGKQRELVAY

ITNGDITNYADSVQGRVIISRDNAKNTVYLHMNSLKPEDTAVYYCYAVGG

RTFWGQGTQVTVSS
```

(Expression of Anti-NP VHH Antibody)

Figure 2:
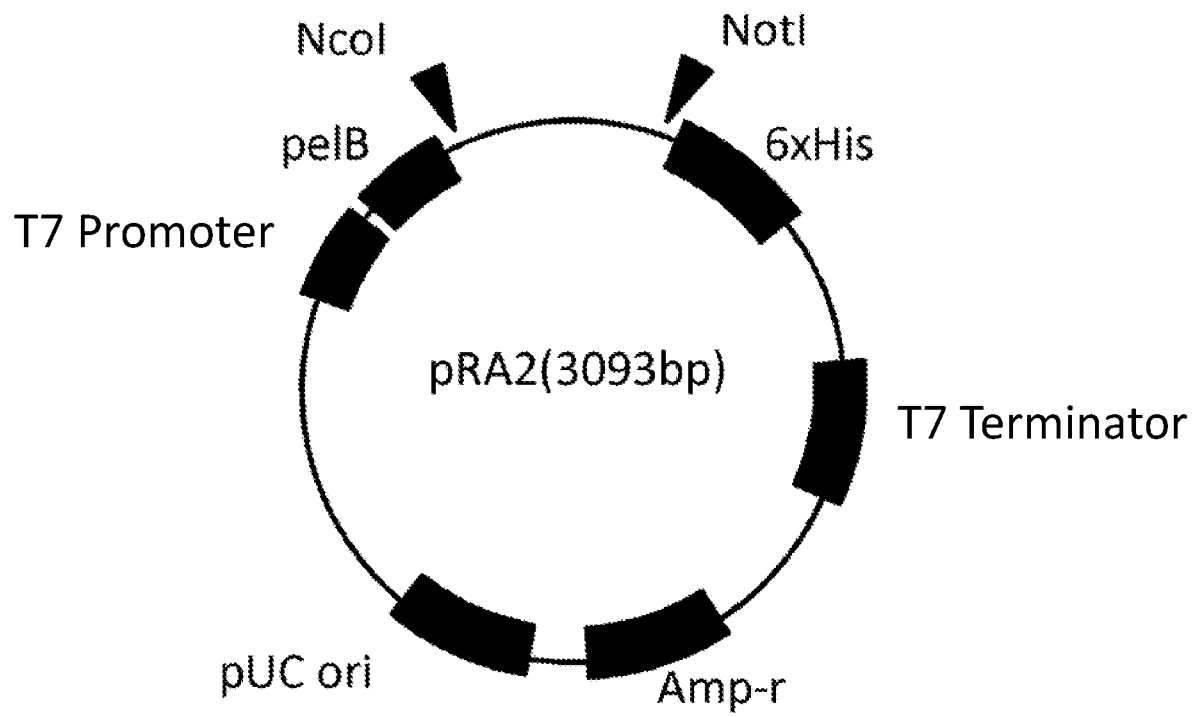
FIG. 2 shows a vector map used to express the VHH antibody.
Figure 3A:
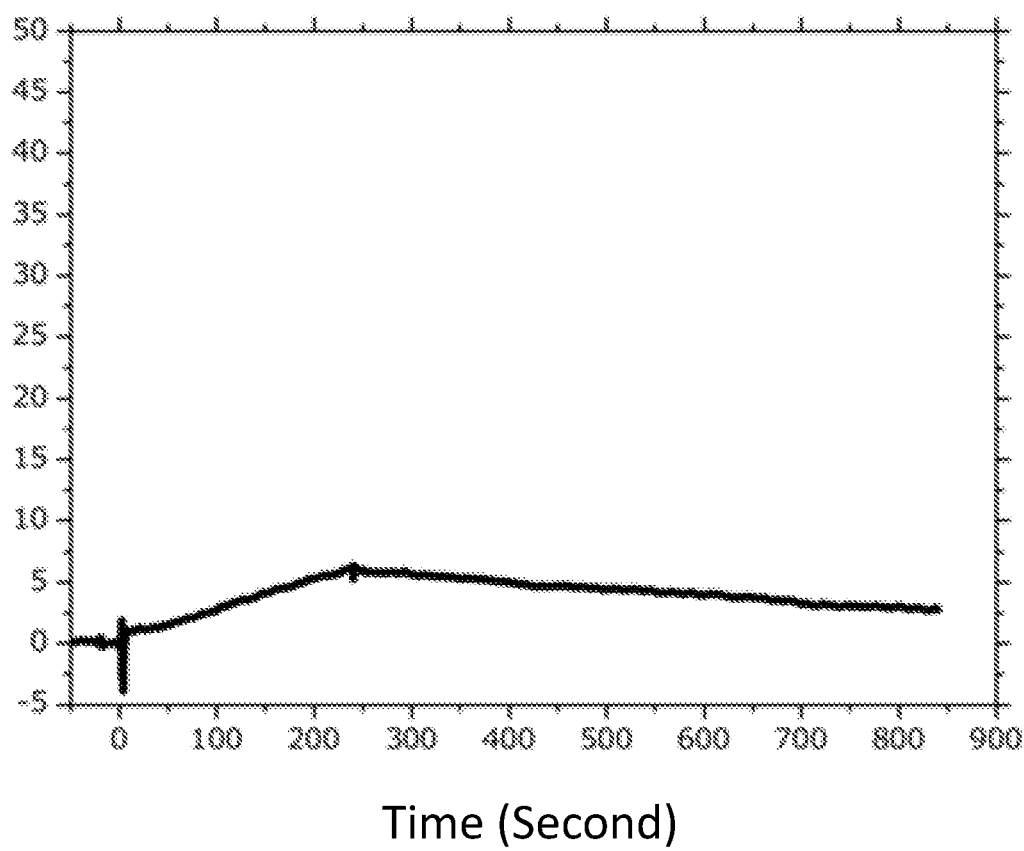
FIG. 3A is a graph showing the results of SPR evaluation of the binding ability of a VHH antibody (concentration: 0.78 nM) containing the amino acid sequence represented by SEQ ID NO: 8 to a recombinant intranuclear protein.
Figure 3B:
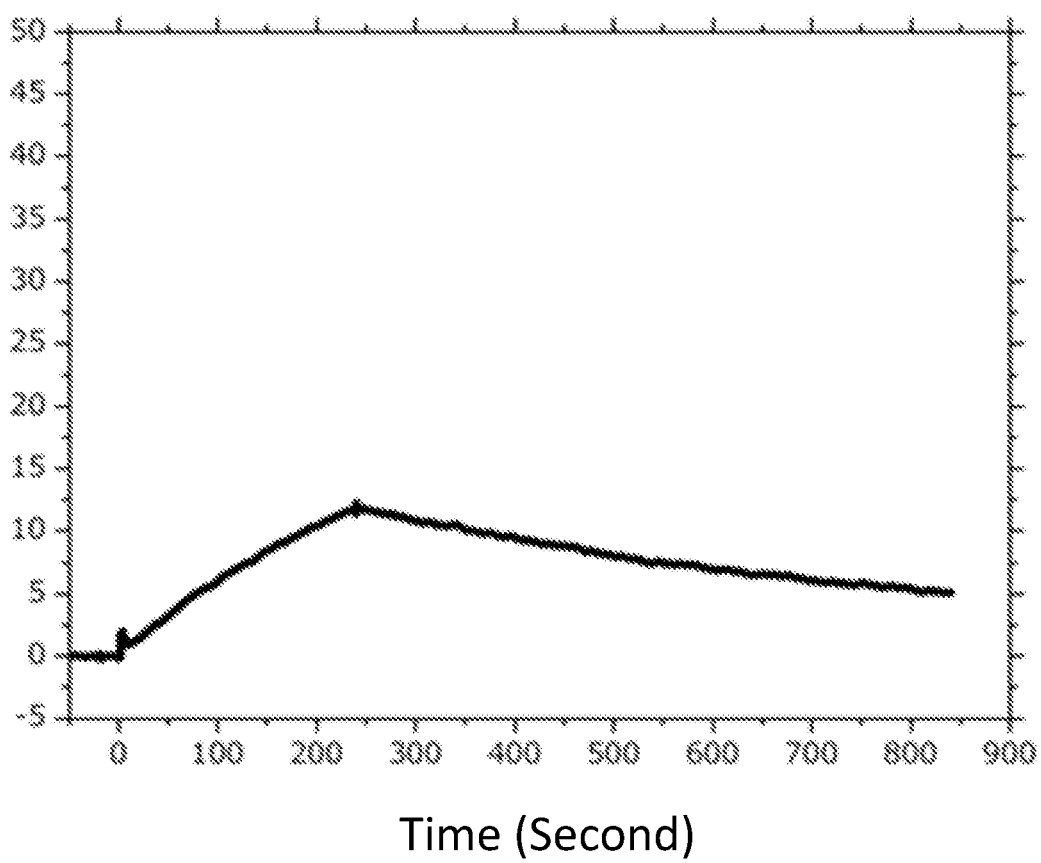
FIG. 3B is a graph showing the results of SPR evaluation of the binding ability of the VHH antibody (concentration: 1.56 nM) containing the amino acid sequence represented by SEQ ID NO: 8 to the recombinant intranuclear protein.
Figure 3C:
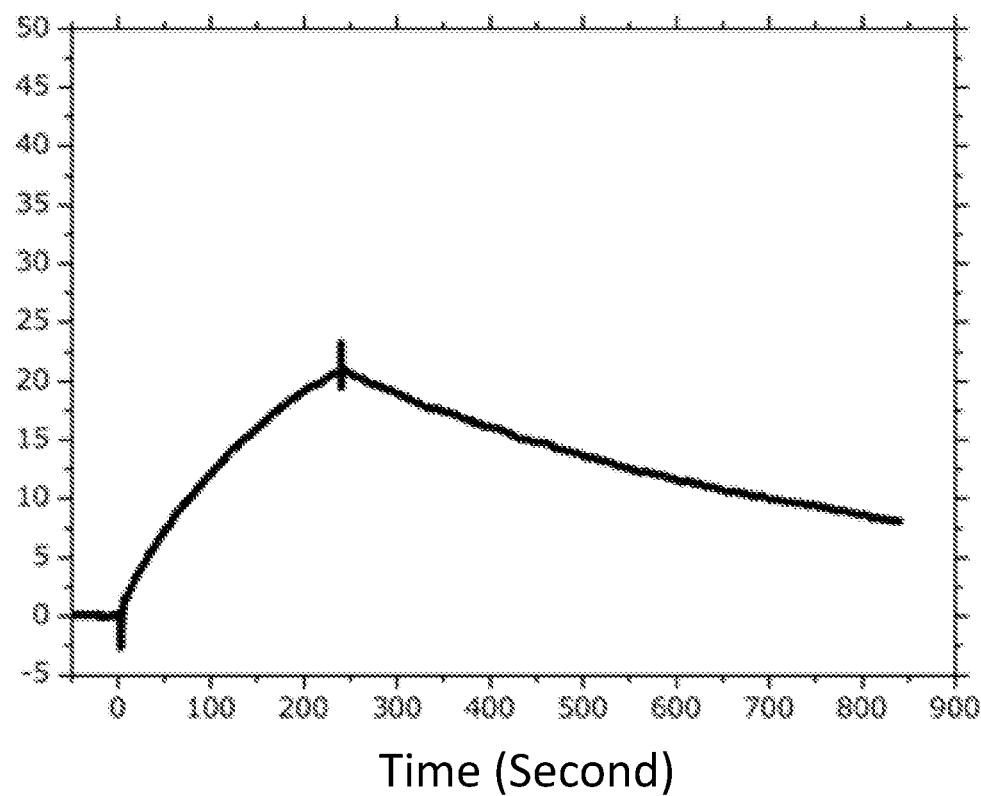
FIG. 3C is a graph showing the results of SPR evaluation of the binding ability of the VHH antibody (concentration: 3.125 nM) containing the amino acid sequence represented by SEQ ID NO: 8 to the recombinant intranuclear protein.
Figure 3D:
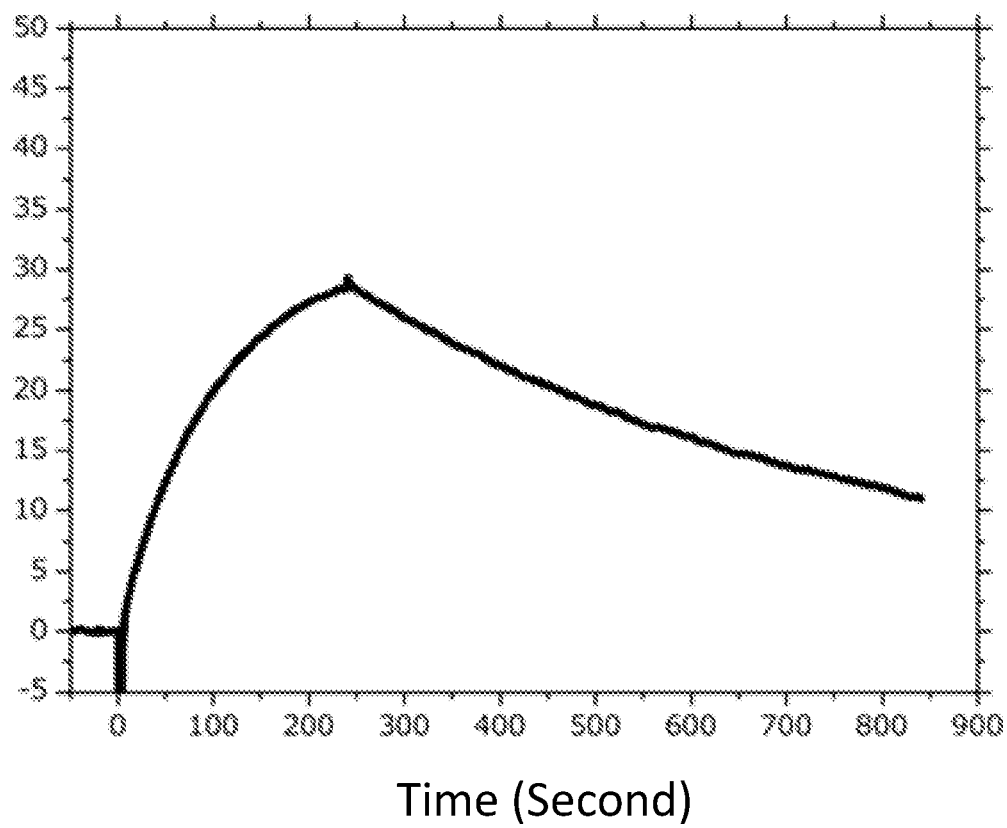
FIG. 3D is a graph showing the results of SPR evaluation of the binding ability of the VHH antibody (concentration: 6.25 nM) containing the amino acid sequence represented by SEQ ID NO: 8 to the recombinant intranuclear protein.
Figure 3E:
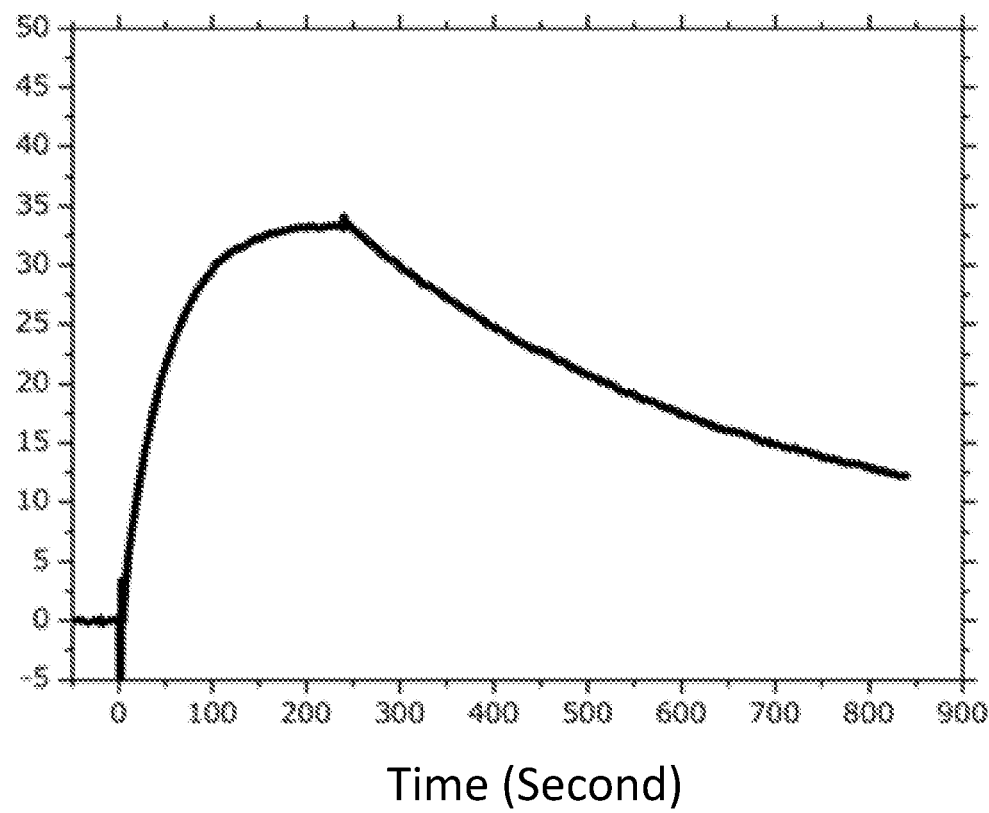
FIG. 3E is a graph showing the results of SPR evaluation of the binding ability of the VHH antibody (concentration: 12.5 nM) containing the amino acid sequence represented by SEQ ID NO: 8 to the recombinant intranuclear protein.
Figure 3F:
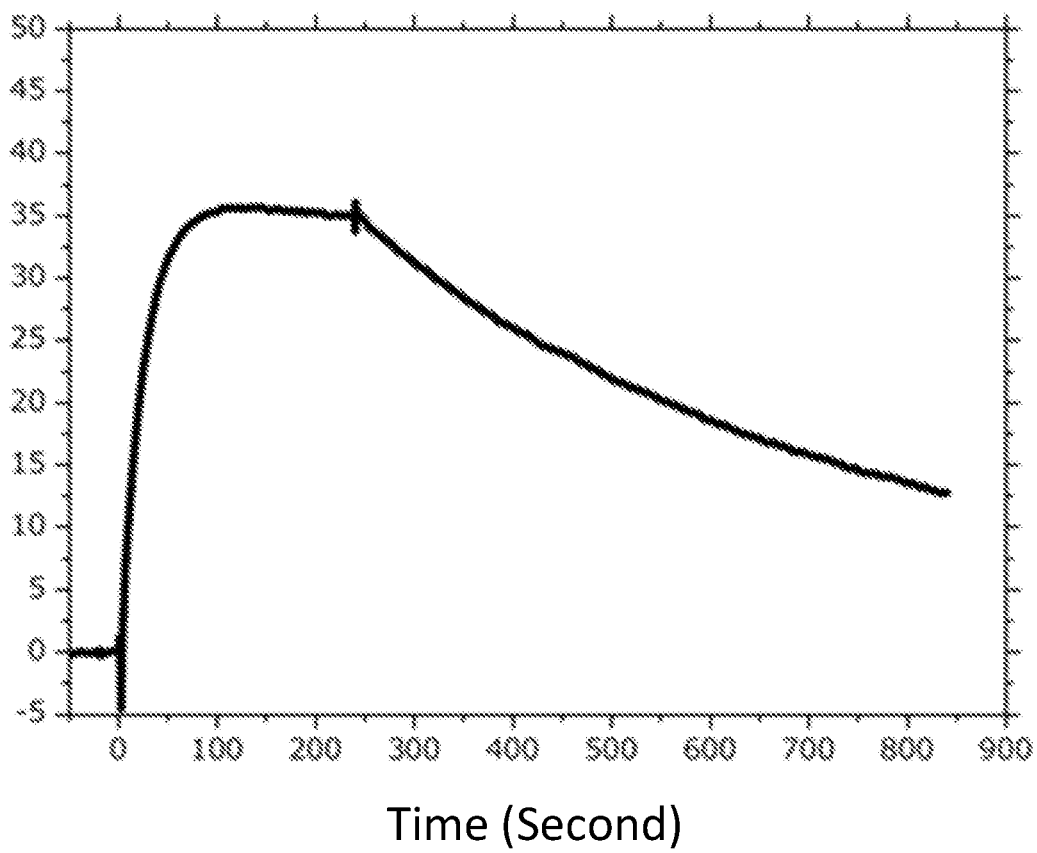
FIG. 3F is a graph showing the results of SPR evaluation of the binding ability of the VHH antibody (concentration: 25 nM) containing the amino acid sequence represented by SEQ ID NO: 8 to the recombinant intranuclear protein.
Figure 4A:
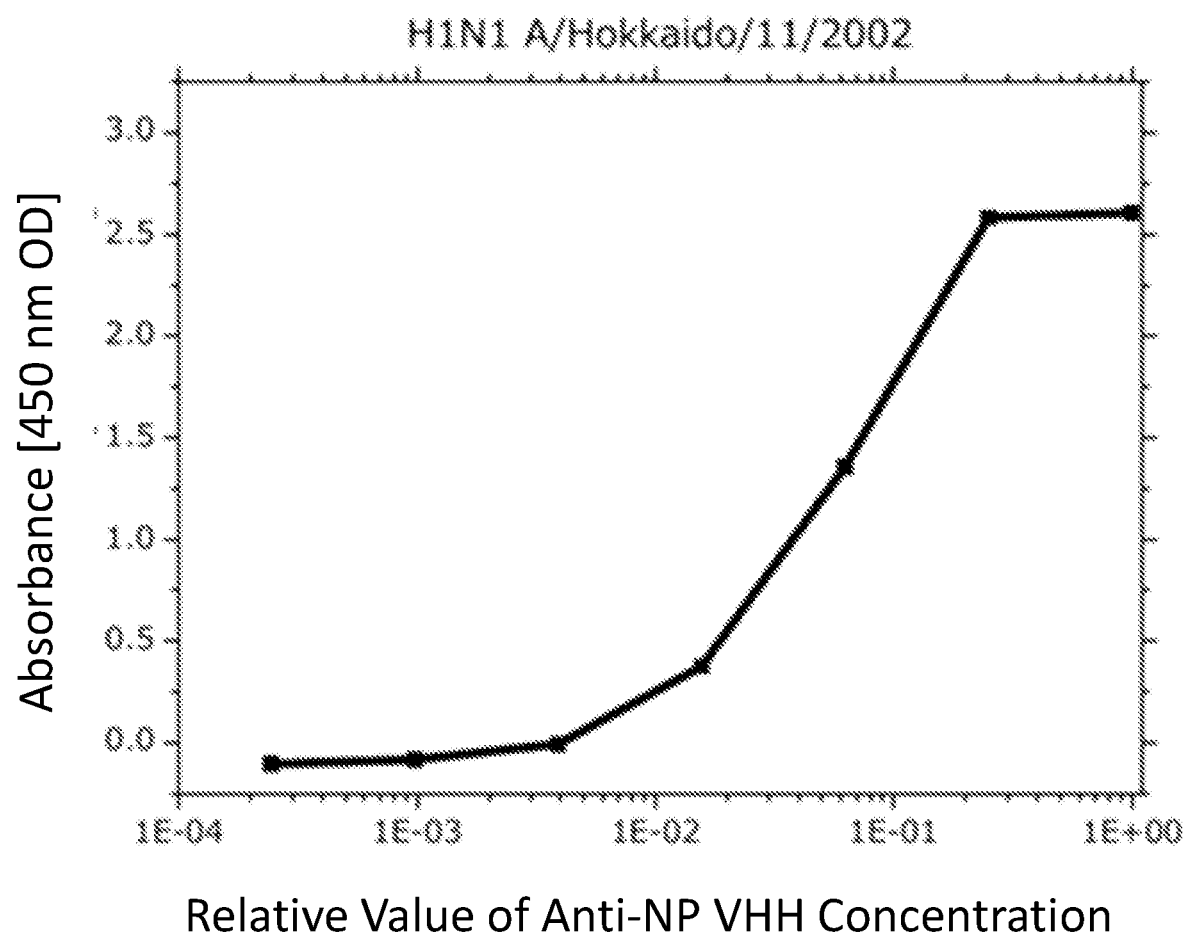
FIG. 4A is a graph showing the measurement results of the cross-reactivity of the VHH antibody containing the amino acid sequence represented by SEQ ID NO: 8 with regard to an influenza virus type A H1N1 A/Hokkaido/11/2002.
Figure 4B:
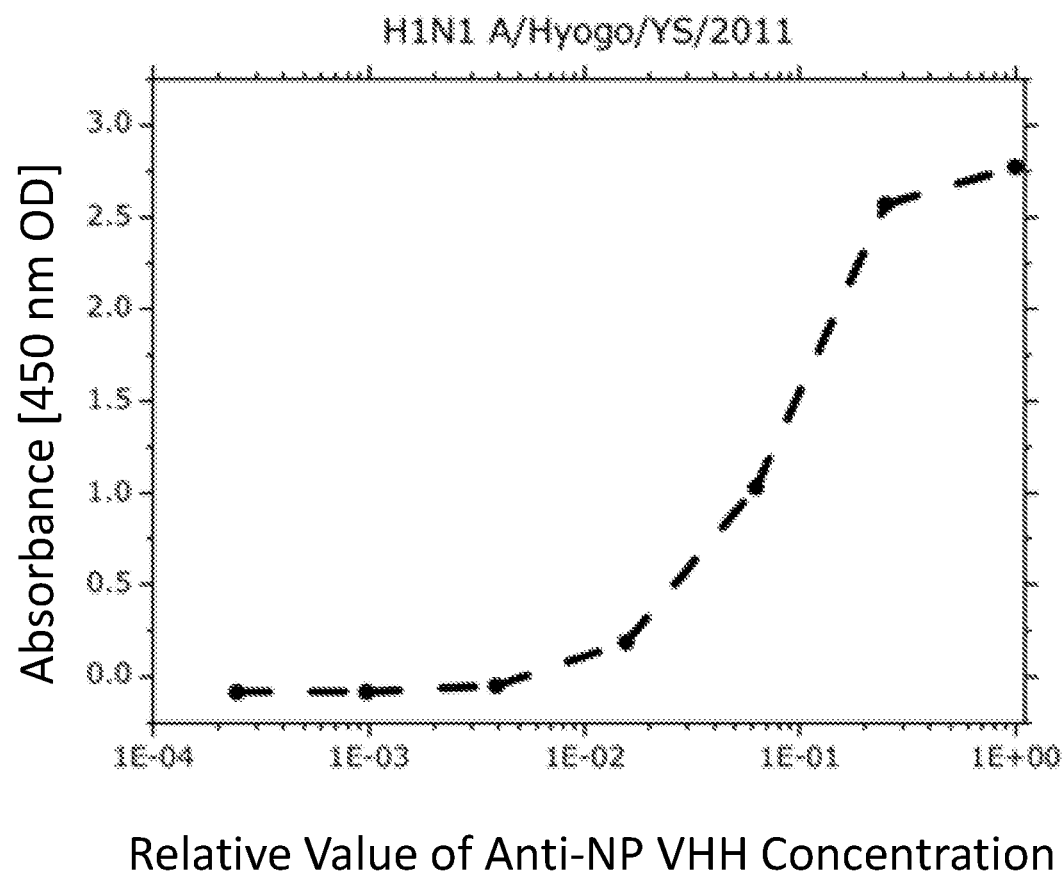
FIG. 4B is a graph showing the measurement results of the cross-reactivity of the VHH antibody containing the amino acid sequence represented by SEQ ID NO: 8 with regard to an influenza virus type A H1N1 A/Hyogo/YS/2011.
Figure 4C:
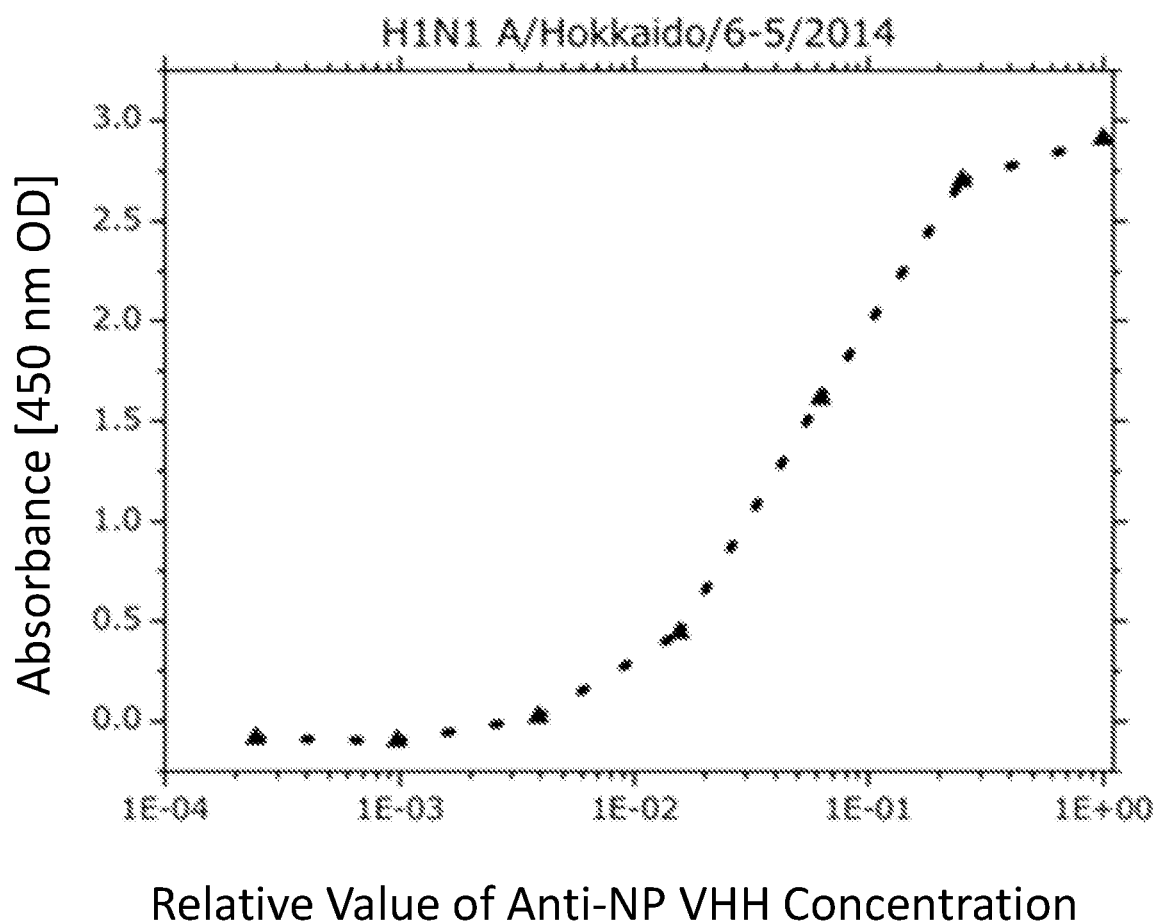
FIG. 4C is a graph showing the measurement results of the cross-reactivity of the VHH antibody containing the amino acid sequence represented by SEQ ID NO: 8 with regard to an influenza virus type A H1N1 A/Hokkaido/6-5/2014.
Figure 4D:
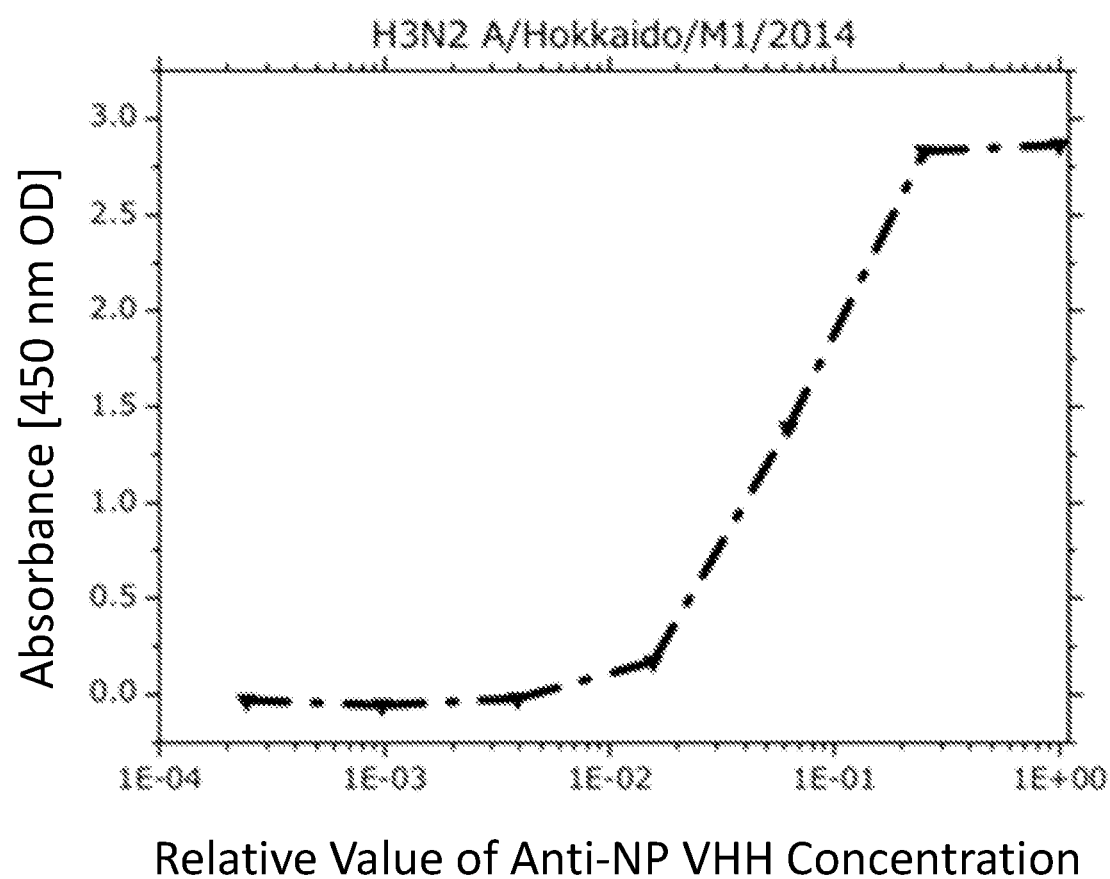
FIG. 4D is a graph showing the measurement results of the cross-reactivity of the VHH antibody containing the amino acid sequence represented by SEQ ID NO: 8 with regard to an influenza virus type A H3N2 A/Hokkaido/M1/2014.
Figure 4E:
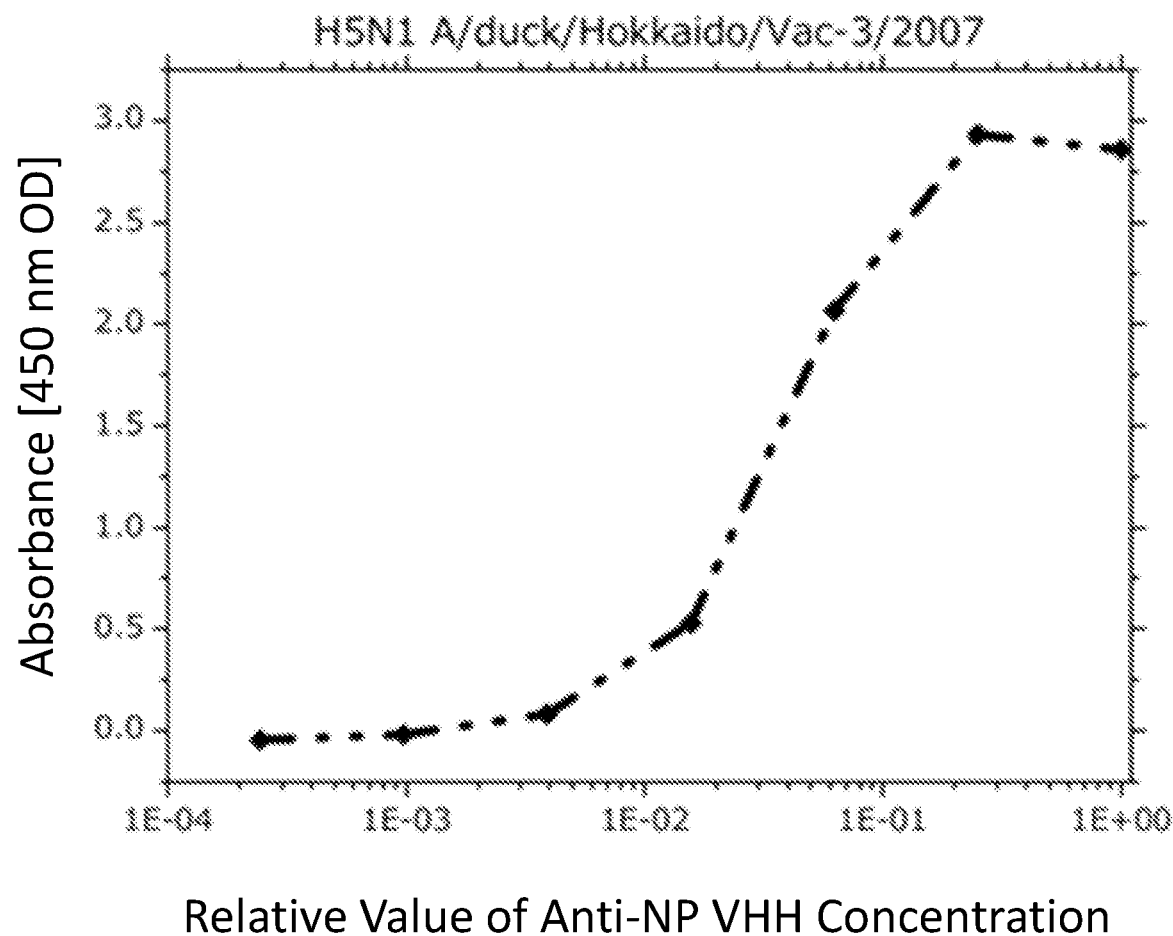
FIG. 4E is a graph showing the measurement results of the cross-reactivity of the VHH antibody containing the amino acid sequence represented by SEQ ID NO: 8 with regard to an influenza virus type A H5N1 A/duck/Hokkaido/Vac-3/2007.
Figure 4G:
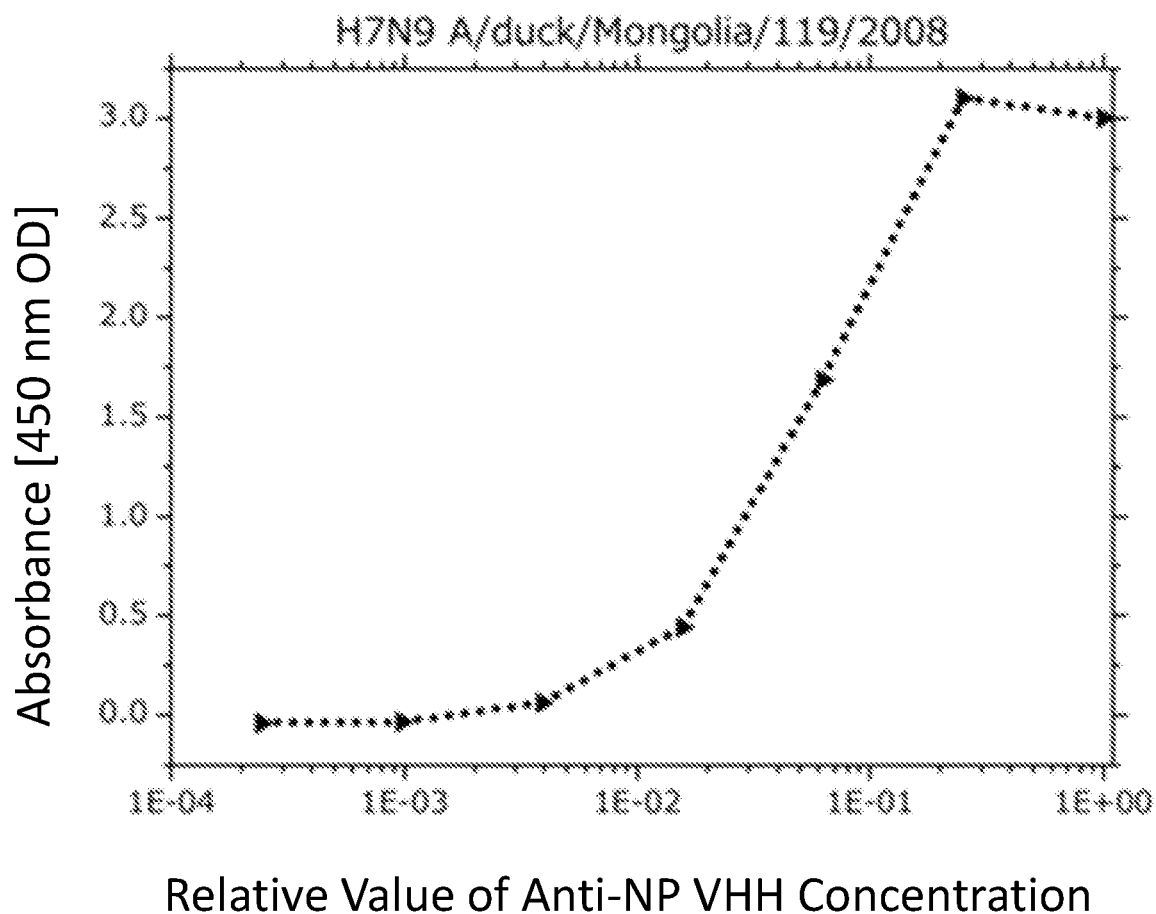
FIG. 4G is a graph showing the measurement results of the cross-reactivity of the VHH antibody containing the amino acid sequence represented by SEQ ID NO: 8 with regard to an influenza virus type A 117N9 A/duck/Mongolia/119/2008.

A vector pRA2(+) was used as an expression vector (see FIG. 2). The vector pRA2(+) was purchased from Merck Millipore Company. Using In-Fusion HD Cloning Kit (available from Takara Bio Inc.), the VHH sequence was ligated into a vector pRA2(+). Hereinafter, the ligation process will be described in more detail.

First, a VHH antibody gene fragment was amplified by the PCR method using the following two primers (SEQ ID NO: 19 and SEQ ID NO: 20) from the plasmid Vector 1 in which the VHH antibody gene fragment included in the gene library of the VHH antibody was ligated. In this way, the following one DNA (SEQ ID NO: 21) including a gene sequence coding for the amino acid sequence represented by the SEQ ID NO: 8 was obtained.

```
Primer 1:
                                        (SEQ ID NO: 19)
5'-CAGCCGGCCATGGCTCAGTTGCAGCTCGTGGAGTCTGGG-3'

Primer 2:
                                        (SEQ ID NO: 20)
5'-ATGGTGTGCGGCCGCTGAGGAGACGGTGACCTGGGTCC-3'

(SEQ ID NO: 21)
5'-CAGCCGGCCATGGCTCAGTTGCAGCTCGTGGAGTCTGGGGAGGCTT

GGTGCAGGCTGGGGGGTCTCTGAGACTCTCCTGTGCAGCCTCTGGAAGCG

CCTTCAGCCTCTATGCCATGGGCTGGCACCGCCAGGCTCCAGGGAAGCAG

CGCGAGTTGGTCGCATATATTACTAATGGTGACATCACAAACTATGCGGA

CTCCGTGCAGGGCCGTGTCATCATCTCCAGAGACAACGCCAAAAACACGG

TGTATCTACACATGAACAGCCTGAAACCTGAGGACACAGCCGTCTATTAT

TGTTATGCAGTGGGGGGTCGGACCTTCTGGGGCCAGGGGACCCAGGTCAC

CGTCTCCTCAGCGGCCGCACACCAT-3'
```

On the other hand, a part of the base sequence included in the vector pRA2 was amplified by a PCR method using the following two primers (SEQ ID NO: 22 and SEQ ID NO: 23). In this way, a DNA (SEQ ID NO: 25) was obtained.

Primer 1:
(SEQ ID NO: 22)
5'-GCGGCCGCACACCATCATCACCACCATTAATAG-3'

Primer 2:
(SEQ ID NO: 23)
5'-AGCCATGGCCGGCTGGGCCGCGAGTAATAAC-3'

(SEQ ID NO: 25)
GCGGCCGCACACCATCATCACCACCATTAATAGcactagtcaagaggatc cggctgctaacaaagcccgaaaggaagctgagttggctgctgccaccgct gagcaataactagcataaccccttggggcctctaaacgggtcttgagggg ttttttgctgaaaggaggaactatatccggatgaattccgtgtattctat agtgtcacctaaatcgtatgtgtatgatacataaggttatgtattaattg tagccgcgttctaacgacaatatgtacaagcctaattgtgtagcatctgg cttactgaagcagaccctatcatctctcgtaaactgccgtcagagtcg gtttggttggacgaaccttctgagtttctggtaacgccgtcccgcacccg gaaatggtcagcgaaccaatcagcagggtcatcgctagccagatcctcta cgccggacgcatcgtggccggcatcaccggcgccacaggtgcggttgctg gcgcctatatcgccgacatcaccgatggggaagatcgggctcgccacttc gggctcatgagcgcttgtttcggcgtgggtatggtggcaggcccgtggc cggggactgttgggcgccatctccttgcatgcaccattccttgcggcgg cggtgctcaacggcctcaacctactactgggctgcttcctaatgcaggag tcgcataagggagagcgtcgaatggtgcactctcagtacaatctgctctg atgccgcatagttaagccagccccgacacccgccaacacccgctgacgcg ccctgacgggcttgtctgctcccggcatccgcttacagacaagctgtgac cgtctccggagctgcatgtgtcagaggttttcaccgtcatcaccgaaac gcgcgagacgaaagggcctcgtgatacgcctattttttataggttaatgtc atgataataatggtttcttagacgtcaggtggcacttttcggggaaatgt gcgcggaacccctatttgtttattttctaaatacattcaaatatgtatc cgctcatgagacaataaccctgataaatgcttcaataatattgaaaaagg aagagtatgagtattcaacatttccgtgtcgcccttattccctttttgc ggcattttgccttcctgttttgctcacccagaaacgctggtgaaagtaa aagatgctgaagatcagttgggtgcacgagtgggttacatcgaactggat ctcaacagcggtaagatccttgagagttttcgccccgaagaacgttttcc aatgatgagcacttttaaagttctgctatgtggcgcggtattatcccgta ttgacgccgggcaagagcaactcggtcgccgcatacactattctcagaat gacttggttgagtactcaccagtcacagaaaagcatcttacggatggcat gacagtaagagaattatgcagtgctgccataaccatgagtgataacactg cggccaacttacttctgacaacgatcggaggaccgaaggagctaaccgct tttttgcacaacatgggggatcatgtaactcgccttgatcgttgggaacc ggagctgaatgaagccataccaaacgacgagcgtgacaccacgatgcctg tagcaatggcaacaacgttgcgcaaactattaactggcgaactacttact ctagcttcccggcaacaattaatagactggatggaggcggataaagttgc aggaccacttctgcgctcggcccttccggctggctggtttattgctgata aatctggagccggtgagcgtgggtctcgcggtatcattgcagcactgggg ccagatggtaagccctcccgtatcgtagttatctacacgacggggagtca ggcaactatggatgaacgaaatagacagatcgctgagataggtgcctcac tgattaagcattggtaactgtcagaccaagtttactcatatatactttag attgatttaaaacttcattttaatttaaaaggatctaggtgaagatcct ttttgataatctcatgaccaaaatcccttaacgtgagttttcgttccact gagcgtcagacccgtagaaaagatcaaaggatcttcttgagatccttt tttctgcgcgtaatctgctgcttgcaaacaaaaaaaccaccgctaccagc ggtggtttgtttgccggatcaagagctaccaactcttttccgaaggtaa ctggcttcagcagagcgcagataccaaatactgttcttctagtgtagccg tagttaggccaccacttcaagaactctgtagcaccgcctacatacctcgc tctgctaatcctgttaccagtggctgctgccagtggcgataagtcgtgtc ttaccgggttggactcaagacgatagttaccggataaggcgcagcggtcg ggctgaacggggggtcgtgcacacagcccagcttggagcgaacgaccta caccgaactgagatacctacagcgtgagctatgagaaagcgccacgcttc ccgaagggagaaaggcggacaggtatccggtaagcggcagggtcggaaca ggagagcgcacgagggagcttccaggggaaacgcctggtatctttatag tcctgtcgggtttcgccacctctgacttgagcgtcgatttttgtgatgct cgtcaggggggcggagcctatggaaaaacgccagcaacgcggcctttta cggttcctggccttttgctggccttttgctcacatgttctttcctgcgtt atccctgattctgtggataaccgtattaccgcctttgagtgagctgata ccgctcgccgcagccgaacgaccgagcgcagcgagtcagtgagcgaggaa gcggaagagcgcccaatacgcaaaccgcctctccccgcgcgttggccgat tcattaatgcagctggcttatcgaaattaatacgactcactatagggaga cccaagctttatttcaaggagacagtcataATGaaatacctattgcctac ggcagccgctggattgttattactcgcggcccagccggccatggct DNAs other than the following two DNAs (I) and (II) were fragmented with a restriction enzyme DpnI (available from TOYOBO). In other words, the following two DNAs (I) and (II) remained unchanged; however, the rest of the DNAs were fragmented.

(I) the DNA represented by SEQ ID NO: 21, and
(II) the DNA represented by SEQ ID NO: 25.

The DNA represented by SEQ ID NO: 21 was fused with the DNA represented by the SEQ ID NO: 25 using In-Fusion HD Cloning Kit (available from Takara Bio Inc.). In this way, the VHH antibody gene fragment was ligated into the vector pRA2(+).

The ligation solution (10 microliters) and coli bacteria JM109 (available from Takara Bio, 100 microliters) were mixed on ice. The mixture solution was left at rest on the ice for thirty minutes. Then, the mixture solution was heated at a temperature of 42 degrees Celsius for forty five seconds. Finally, the mixture solution was left at rest on the ice for three minutes. This procedure is known as a general heat shock method.

After the incubation at a temperature of 37 degrees Celsius for one hour with shaking, the total amount of the mixture solution was distributed onto an LBA culture medium containing ampicillin at a concentration of 100 micrograms/milliliter. The LBA culture medium was left at rest overnight at a temperature of 37 degrees Celsius.

Three colonies were selected from among the colonies formed on the LBA culture medium. The selected three colonies were incubated overnight in the LBA culture medium (3 milliliters).

The plasmids contained in the incubated coli bacteria were extracted from the LBA culture medium using a plasmid extraction kit (available from Sigma, trade name: Gene Elute Plasmid Mini Kit). In order to confirm that the gene of the targeted VHH antibody was inserted in the plasmid, the sequence of the plasmid was analyzed by Greiner Company. For the analysis of the sequence, a general T7 promoter primer set was used.

Selected were plasmids which were confirmed through the analysis of the sequence to have been formed as planned.

Coli bacteria (Competent Cell BL21 (DE3) pLysS, available from Life Technologies Company) were transfected with the selected plasmids by a heat shock method.

An LBA culture medium (1 milliliter) was injected into the solution containing the transfected coli bacteria. Then, the coli bacteria were recovered at a temperature of 37 degrees Celsius for one hour, while shaken at 213 rpm.

Then, the coli bacteria solution was collected. The collected coli bacteria solution (1 milliliter) was distributed onto an LBA culture medium. The LBA culture medium was left at rest overnight at a temperature of 37 degrees Celsius.

One colony was selected from among the colonies formed in the LBA culture medium. The selected colony was picked up with a toothpick. The picked-up colony was incubated in an LBA culture medium (3 milliliters) at a temperature of 37 degrees Celsius, while shaken at 213 rpm. In this way, a culture liquid was obtained.

In addition, the culture liquid (3 milliliters) was mixed with an LBA culture medium (1,000 milliliters). Until the absorbance of the mixture solution at a wavelength of 600 nanometers reached 0.6, the mixture solution was shaken at 120 rpm at a temperature of 28 degrees Celsius.

After the absorbance reached 0.6, an isopropylthiogalactoside solution (hereinafter, referred to as "IPTG solution") was added to the mixture solution. The final concentration of the IPTG solution was 0.5 mM. The coli bacteria contained in the mixture solution were incubated at a temperature of 20 degrees Celsius overnight. In order to collect the thus-incubated coli bacteria, the mixture solution was subjected to centrifugation at 6,000 rpm at a temperature of 4 degrees Celsius for ten minutes.

The collected coli bacteria were mixed with a mixture solvent containing 50 mM Tris-HCl, 500 mM NaCl, and 5 mM imidazole. The mixture solvent had a volume of 50 milliliters. The coli bacteria contained in the mixture solution were disintegrated with an ultrasonic wave.

The disintegration liquid containing coli bacteria was subjected to centrifugation at 40,000 g at a temperature of 4 degrees Celsius for thirty minutes to obtain an eluate. The supernatant was collected. The collected supernatant was filtered through a 0.45-micrometer filter.

The filtrate was purified with Ni-NTA-Agarose (available from QIAGEN) in accordance with recommended protocol. For the purification, an elution buffer having a total amount of 3 milliliters was used for 1 milliliter of Ni-NTA-Agarose.

Furthermore, the eluate containing the anti-NP antibody was purified with a column chromatograph (available from General Electric Company, trade name: Akta purifier). In this way, a solution containing the anti-NP antibody was obtained.

The anti-NP antibody contained in the thus-obtained solution was quantified with an absorption spectrometer (available from Scrum Inc., trade name: nanodrop) on the basis of the absorption measurement value at a wavelength of 280 nanometers. As a result, the concentration of the anti-NP antibody was 1.30 milligrams/milliliter.

(D-1) Surface Plasmon Resonance Evaluation of Anti-NP Antibody Using Recombinant NP The anti-NP antibody was evaluated as below with a recombinant NP and a surface plasmon resonance evaluation device. The details of the surface plasmon resonance (hereinafter, referred to as "SPR") will be described below.

SPR evaluation device: T200 (available from GE Healthcare)

Immobilization buffer: PBS containing 0.05% of Tween 20

Running buffer: PBS containing 0.05% of Tween 20

Sensor chip: CM5 (available from GE Healthcare)

Immobilization reagents: N-hydroxysuccinimide (NHS) and ethyl (dimethylaminopropyl) carbodiimide (EDC)

Anti-Flag antibody: Monoclonal ANTI-FLAG antibody (available from SIGMA)

NP: recombinant nucleoprotein (NP) protein derived from influenza virus H1N1 to which a Flag tag was fused and which was prepared using baculovirus.

The anti-Flag antibody was immobilized in accordance with the wizard included in the control software of the SPR evaluation device T200. For the immobilization of the anti-Flag antibody, an acetic acid solution having a pH of 5.0 was used.

The anti-NP antibody consisting of the amino acid sequence represented by SEQ ID NO: 8 was used as an analyte. In the first to sixth analyses, the concentrations of the anti-NP antibody contained in the running buffer were adjusted to 0.78 nM, 1.56 nM, 3.125 nM, 6.25 nM, 12.5 nM, and 25 nM, respectively. First, the recombinant intranuclear proteins were captured with the anti-Flag antibodies. Then, the anti-NP antibodies were supplied. In this way, the anti-NP antibodies were evaluated. FIGS. 3A-3F are graphs showing an evaluation result outputted from the SPR evaluation device T200. The dissociation constant Kd was calculated using the evaluation software (available from GE Healthcare). As a result, the dissociation constant Kd was 1.09 nM.

(D-2) Evaluation of Cross-reactivity to Other Influenza Virus Subtypes

Next, in order to evaluate binding ability of the VHH antibody including the amino acid sequence represented by SEQ ID NO: 8 with nucleoproteins (namely, NPs) derived from a type-A influenza virus subtypes H1N1 (A/Hokkaido/11/2002), H1N1 (A/Hyogo/YS/2011), H1N1 (A/Hokkaido/6-5/2014), H3N2 (A/Hokkaido/M1/2014), H5N1 (A/duck/Hokkaido/Vac-3/2007), H7N7 (A/duck/Hokkaido/Vac-2/2004), and H7N9 (A/duck/Mongolia/119/2008), the binding ability to a virus solution containing the intranuclear proteins was evaluated by an ELISA measurement method.

The virus solution including the intranuclear protein derived from the type-A influenza virus subtype H1N1 (A/Hokkaido/11/2002) was prepared. The virus solution was obtained from School/Faculty of Veterinary Medicine, Hokkaido University.

Similarly, six virus solutions including the intranuclear proteins derived from the type-A influenza virus subtypes H1N1 (A/Hyogo/YS/2011), H1N1 (A/Hokkaido/6-5/2014), H3N2 (A/Hokkaido/M1/2014), H5N1 (A/duck/Hokkaido/Vac-3/2007), H7N7 (A/duck/Hokkaido/Vac-2/2004), and H7N9 (A/duck/Mongolia/119/2008) were prepared. The six virus solutions were obtained from School/Faculty of Veterinary Medicine, Hokkaido University.

Furthermore, a virus solution including the intranuclear protein derived from the type-B influenza virus (B/Hokkaido/30-4/2014) was prepared. The virus solution was obtained from School/Faculty of Veterinary Medicine, Hokkaido University.

A part of a solution A (concentration 10 micrograms/milliliter) containing the VHH antibody including the amino acid sequence represented by SEQ ID NO: 8 was diluted 4-fold with a PBS containing both 3% skim milk (available from Wako Pure Chemical Industries, Ltd.) and 0.05% Tween 20. Hereinafter, the PBS containing both 3% skim milk and 0.05% Tween 20 is referred to as "skim-milk-containing PBST". In this way, a diluted solution B (concentration: 2.5 micrograms/milliliter) of the solution containing the VHH antibody including the amino acid sequence represented by SEQ ID NO: 8 was provided. This was repeated to provide a diluted solution C (concentration: 0.625 micrograms/milliliter), a diluted solution D (concentration: 0.15625 micrograms/milliliter), a diluted solution E (concentration: 0.0390625 micrograms/milliliter), a diluted solution F (concentration: $9.76562\times10^{-4}$ micrograms/milliliter), and a diluted solution G (concentration: $2.44141\times10^{-4}$ micrograms/milliliter).

The virus solutions including the intranuclear proteins derived from the type-A influenza virus subtypes H1N1 (A/Hokkaido/11/2002), H1N1 (A/Hyogo/YS/2011), H1N1 (A/Hokkaido/6-5/2014), H3N2 (A/Hokkaido/M1/2014), H5N1 (A/duck/Hokkaido/Vac-3/2007), H7N7 (A/duck/Hokkaido/Vac-2/2004), H7N9 (A/duck/Mongolia/119/2008), and the type-B influenza virus (B/Hokkaido/30-4/2014) were injected into the wells of 96-well plate (Maxisorp, Nunc). Each of the wells contained 50 microliters of the solution. The 96-well plate was left at rest at room temperature for two hours to immobilize the virus in the wells.

The skim-milk-containing PBST was injected into each well to block the virus. The volume of the PBST injected into each well was 200 microliters. The 96-well plate was left at rest at room temperature for three hours.

PBST containing 0.05% Tween 20 was injected into each well to wash the wells. The PBST had a pH of 7.4. The volume of the PBST injected into each well was 200 microliters. This was repeated three times.

Each of the diluted solutions of the VHH antibody including the amino acid sequence represented by SEQ ID NO: 8 included in the diluted solutions A-G was injected into each well. As a reference, the skim-milk-containing PBST was injected into another well. This well including the skim-milk-containing PBST only was used as a reference to remove a background in measurement. The volume of the solutions injected into each well was 50 microliters. The 96-well plate was left at rest at room temperature. In this way, the VHH antibodies included in the diluted solutions A-G were bound to the intranuclear protein contained in the wells. The 96-well plate was left at rest at room temperature for one hour.

PBST containing 0.05% Tween 20 was injected into each well to wash the wells. The PBST had a pH of 7.4. The volume of the PBST injected into each well was 200 microliters. This was repeated five times.

Labelled antibodies (available from Medical and Biological laboratories Co., Ltd, trade name: Anti-His-tag mAb-HRP-DirecT) were diluted 10,000-fold with PBST containing 0.05% Tween 20. The thus-diluted labelled antibodies were injected into each well (50 microliters/well). Then, the 96-well plate was left at rest for one hour.

PBST containing 0.05% Tween 20 was injected into each well to wash the wells. The PBST had a pH of 7.4. The volume of the PBST injected into each well was 200 microliters. This was repeated five times.

The color-producing agent (available from Thermo Scientific, trade name: 1-step ultra TMB-ELISA) was injected into each well (50 microliters/well). The 96-well plate was left at rest for thirty minutes to cause the color-producing agent to react with the antibody.

A color-stopping agent (available from ScyTek laboratories, trade name: TMB Stop Buffer) containing sulfuric acid and hydrochloric acid at a low concentration was injected into each well at a concentration of 50 microliters/well to cease the reaction.

The absorbance of the solution at a wavelength of 450 nanometers was measured. FIGS. 4A-4H are graphs showing the measurement results of the cross reaction of the VHH antibody including the amino acid sequence represented by SEQ ID NO: 8 with the type-A influenza virus subtypes H1N1 (A/Hokkaido/11/2002), H1N1 (A/Hyogo/YS/2011), H1N1 (A/Hokkaido/6-5/2014), H1N2 (A/Hokkaido, M1/2014), H5N1 (A/duck/Hokkaido/Vac-3/2007), H7N7 (A/duck/Hokkaido/Vac-2/2004), H7N9 (A/duck/Mongolia/19/2008), and the type-B influenza virus, respectively.

As understood from FIGS. 4A-4H, the VHH antibody including the amino acid sequence represented by SEQ ID NO: 8 has high cross-reactivity with the intranuclear proteins derived from the type-A influenza virus subtypes H1N1 (A/Hokkaido/11/2002), H1N1 (A/Hyogo/YS/2011), H1N1 (A/Hokkaido/6-5/2014), H3N2 (A/Hokkaido/M1/2014), H5N1 (A/duck/Hokkaido/Vac-3/2007), H7N7 (A/duck/Hokkaido/Vac-2/2004), and H7N9 (A/duck/Mongolia/119/2008). On the other hand, the VHH antibody including the amino acid sequence represented by SEQ ID NO: 8 has low cross-reactivity with the type-B influenza virus.

Inventive Example 2

Analysis of Antigen Binding Region with HDX-MS

Preparation of Measurement Sample

Purified Anti-NP

The VHH antibody and the NP antigen were dialyzed with a phosphate buffered saline (PBS, pH 7.4) to replace a solvent. An antigen was prepared so as to be 1 mg/mL, and an antibody was added so as to have an equimolar amount to prepare an antigen-antibody complex solution. At the time of concentration, Amicon Ultra-4 Centrifugal Filter Units 3K (Millipore) was used, and aggregates were removed using Nanosep (SIGMA) from the concentrated sample.

Deuteration Conditions

In this study, 60 seconds, 600 seconds, 1800 seconds, 3600 seconds, 7200 seconds, 10800 seconds, and 14400 seconds are selected as a period for labeling with deuterium, and 4M Gdn-HCl, 0.5M TCEP, 200 mM citric acid, pH 2.5 was selected as a quenching solvent to stop deuteration. A deuterium solution was prepared by adding Deuterium Oxide 99.8 atom % D (Tokyo Kasei) to a mixture of reagents so as to have a composition of PBS (pH 7.4).

Measurement Method

HDX-MS measurement was performed with an apparatus owned by Thermo Fisher SCIENTIFIC. The deuterated sample was passed through a pepsin enzyme-immobilized column, and MS measurement was performed immediately after the fragmentation treatment. MS results were analyzed using HDExaminer. A mass spectrometer: Q Exactive Plus (Thermo Fisher Scientific), LC pump: UltiMate 3000 RSnano (Thermo Fisher Scientific), and Auto Sampler: HDx-3 PAL (LEAP Technologies) were used for the MS and autosampler devices. As columns, a digestion column: Poroszyme Immobilized Pepsin Cartridge, 2.1×30 mm (Thermo-Scientific), a desalting column: Acclaim PepMap300 C18 5 um, 1.0 mm×15 mm (ThermoScientic), and an analysis column: Hypersil Gold column, 50×1 mm, 1.9 um (ThermoScientific) were used.

Results

Figure 5:
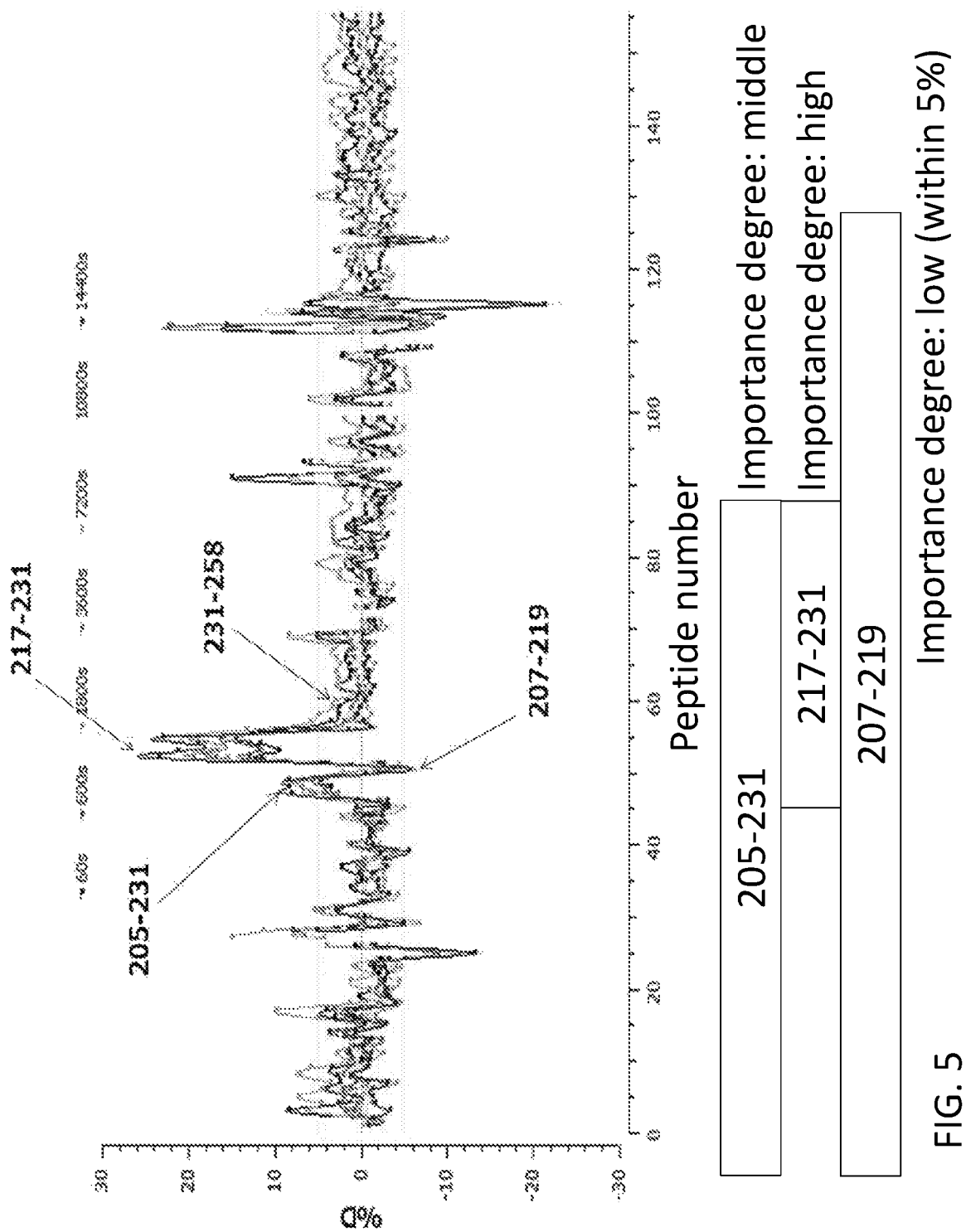
FIG. 5 shows the results of an antigen binding region analysis of HDX-MS. The result of subtracting the deuterium exchange rate of the complex from the deuterium exchange rate of the monomer is shown. The horizontal axis indicates the peptide number, and the vertical axis indicates the deuterium exchange rate.

FIG. 5 shows the results of an antigen binding region analysis of HDX-MS provided by subtracting the deuterium exchange rate of the complex from the deuterium exchange rate of the monomer. Peptides each having a large difference of the deuterium exchange rate have been shown. The difference was positively large with regard to the peptide consisting of the 205th-231st amino acid sequence of SEQ ID NO: 24 and the peptide consisting of the 217th-231st amino acid sequence of SEQ ID NO: 24. The difference was negatively large with regard to the peptide consisting of the 207th-219th amino acid sequence of SEQ ID NO: 24 and the peptide consisting of the 231st-258th amino acid sequence of SEQ ID NO: 24. From the above, it was suggested that the peptide consisting of the 205th-231st amino acid sequence of SEQ ID NO: 24 contains an epitope recognized by the antibody. It was also suggested that the peptide consisting of the 220th-231st amino acid sequence in SEQ ID NO: 24 contains an epitope recognized by the antibody. Therefore, the 205th-231st amino acid sequence of SEQ ID NO: 24 or the 220th-231st amino acid sequence in SEQ ID NO: 24 would be a sequence including the epitope of anti-NP VHH antibody capable of binding to the NP antigen.

INDUSTRIAL APPLICABILITY

The present disclosure provides an antibody capable of binding to an intranuclear protein of an influenza virus and the application thereof.

The invention claimed is:

1. An antibody or antibody derivative comprising a variable domain comprising:
   (a) a complementarity determining region 1 (CDR1) comprising the amino acid sequence of SEQ ID NO: 1,
   (b) a complementarity determining region 2 (CDR2) comprising the amino acid sequence of SEQ ID NO: 2, and
   (c) a complementarity determining region 3 (CDR3) comprising the amino acid sequence of SEQ ID NO: 3;

wherein the antibody or antibody derivative is capable of specifically binding to a protein comprising either:
   (i) amino acid residues 205-231 of SEQ ID NO: 24, or
   (ii) amino acid residues 220-231 of SEQ ID NO: 24.

2. The antibody or antibody derivative of claim 1, wherein the antibody or antibody derivative does not exhibit antigen cross-reactivity or has low cross-reactivity with an intranuclear protein of influenza virus other than a type-A influenza virus.

3. The antibody or antibody derivative of claim 1, wherein the antibody or antibody derivative does not exhibit antigen cross-reactivity or has low cross-reactivity with a intranuclear protein of type-B influenza virus.

4. The antibody or antibody derivative of claim 1, wherein the antibody or antibody derivative is selected from an Fab derivative, an F(ab')2 derivative, an Fv fragment derivative and a VHH antibody.

5. The antibody or antibody derivative of claim 2, wherein the type-A influenza virus is selected from type-A influenza virus of subtypes H1N1, H3N2, H5N1, H7N7 and H7N9.

6. The antibody or antibody derivative of claim 2, wherein the antibody or antibody derivative is operably coupled to a carrier.

7. The antibody or antibody derivative of claim 6, wherein the carrier is selected from a plate, a bead, a disk, a tube, a filter, and a thin film.

8. The antibody or antibody derivative of claim 1, wherein the antibody or antibody derivative is operably coupled to a labeling substance.

9. The antibody or antibody derivative of claim 8, wherein the labeling substance is selected from the group consisting of a fluorescent substance, a luminescent substance, a dye, an enzyme, and a radioactive substance.

10. A device for detecting an intranuclear protein of a type-A influenza virus in an analyte, the device comprising:

(a) an antibody or antibody derivative of claim 1, said antibody or antibody derivative operably coupled to a carrier or a labeling substance; and (b) a detection apparatus for the detection of a change in a physical quantity associated with the carrier or labeling substance resulting from formation of a complex between the antibody or antibody derivative and the intranuclear protein of a type-A influenza virus in the analyte.

11. The device of claim 10, wherein the detection apparatus comprises an enzyme immunoassay, enzyme-linked immunosorbent assay (ELISA), enzyme immunoassay (EIA), radioimmunoassay (RIA), immunochromatography, latex agglutination, fluorescence immunoassay or surface plasmon resonance measurement.

12. The device of claim 10, wherein the physical quantity is selected from emission intensity, chromaticity, light transmittance, turbidity, absorbance and radiation dose.

13. The device of claim 10, wherein the detection apparatus is selected from photometers, spectrometers and dosimeters.

14. A method for detecting an intranuclear protein of a type-A influenza virus in an analyte, the method comprising:

(a) providing an antibody or antibody derivative of claim 1, said antibody or antibody derivative operably coupled to a carrier or a labeling substance;

(b) exposing the antibody or antibody derivative of (a) to the analyte under conditions whereby a complex comprising the antibody or antibody derivative and the intranuclear protein of a type-A influenza virus will form, if present; and (c) detecting a change in a physical quantity based on formation of the complex, thereby detecting the intranuclear protein of the type-A influenza virus in the analyte.

* * * * *

```
                        SEQUENCE LISTING

<160> NUMBER OF SEQ ID NOS: 25

<210> SEQ ID NO 1
    <211> LENGTH: 10
    <212> TYPE: PRT
    <213> ORGANISM: Vicugna pacos

<400> SEQUENCE: 1

Gly Ser Ala Phe Ser Leu Tyr Ala Met Gly
    1               5                   10

<210> SEQ ID NO 2
    <211> LENGTH: 16
    <212> TYPE: PRT
    <213> ORGANISM: Vicugna pacos

<400> SEQUENCE: 2

Tyr Ile Thr Asn Gly Asp Ile Thr Asn Tyr Ala Asp Ser Val Gln Gly
    1               5                   10                  15

<210> SEQ ID NO 3
    <211> LENGTH: 6
    <212> TYPE: PRT
    <213> ORGANISM: Vicugna pacos

<400> SEQUENCE: 3

Val Gly Gly Arg Thr Phe
    1               5

<210> SEQ ID NO 4
    <211> LENGTH: 25
    <212> TYPE: PRT
    <213> ORGANISM: Vicugna pacos

<400> SEQUENCE: 4

Gln Leu Gln Leu Val Glu Ser Gly Gly Gly Leu Val Gln Ala Gly Gly
    1               5                   10                  15

Ser Leu Arg Leu Ser Cys Ala Ala Ser
                20                  25

<210> SEQ ID NO 5
    <211> LENGTH: 14
    <212> TYPE: PRT
```

<213> ORGANISM: Vicugna pacos

<400> SEQUENCE: 5

Trp His Arg Gln Ala Pro Gly Lys Gln Arg Glu Leu Val Ala
1               5                   10

<210> SEQ ID NO 6
<211> LENGTH: 32
<212> TYPE: PRT
<213> ORGANISM: Vicugna pacos

<400> SEQUENCE: 6

Arg Val Ile Ile Ser Arg Asp Asn Ala Lys Asn Thr Val Tyr Leu His
1               5                   10                  15

Met Asn Ser Leu Lys Pro Glu Asp Thr Ala Val Tyr Tyr Cys Tyr Ala
            20                  25                  30

<210> SEQ ID NO 7
<211> LENGTH: 11
<212> TYPE: PRT
<213> ORGANISM: Vicugna pacos

<400> SEQUENCE: 7

Trp Gly Gln Gly Thr Gln Val Thr Val Ser Ser
1               5                   10

<210> SEQ ID NO 8
<211> LENGTH: 114
<212> TYPE: PRT
<213> ORGANISM: Vicugna pacos

<400> SEQUENCE: 8

Gln Leu Gln Leu Val Glu Ser Gly Gly Gly Leu Val Gln Ala Gly Gly
1               5                   10                  15

Ser Leu Arg Leu Ser Cys Ala Ala Ser Gly Ser Ala Phe Ser Leu Tyr
            20                  25                  30

Ala Met Gly Trp His Arg Gln Ala Pro Gly Lys Gln Arg Glu Leu Val
        35                  40                  45

Ala Tyr Ile Thr Asn Gly Asp Ile Thr Asn Tyr Ala Asp Ser Val Gln
    50                  55                  60

Gly Arg Val Ile Ile Ser Arg Asp Asn Ala Lys Asn Thr Val Tyr Leu
65                  70                  75                  80

His Met Asn Ser Leu Lys Pro Glu Asp Thr Ala Val Tyr Tyr Cys Tyr
                85                  90                  95

Ala Val Gly Gly Arg Thr Phe Trp Gly Gln Gly Thr Gln Val Thr Val
            100                 105                 110

Ser Ser

<210> SEQ ID NO 9
<211> LENGTH: 15
<212> TYPE: DNA
<213> ORGANISM: Artificial Sequence
<220> FEATURE:
<223> OTHER INFORMATION: Primer

<400> SEQUENCE: 9
ggtggtcctg gctgc                                                15

<210> SEQ ID NO 10
<211> LENGTH: 50
<212> TYPE: DNA

```
<213> ORGANISM: Artificial Sequence
<220> FEATURE:
<223> OTHER INFORMATION: Primer

<400> SEQUENCE: 10
ctgctcctcg cggcccagcc ggccatggct sagktgcagc tcgtggagtc          50

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
tggggtcttc gctgtggtgc g                                         21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
ttgtggtttt ggtgtcttgg g                                         21

<210> SEQ ID NO 13
<211> LENGTH: 45
<212> TYPE: DNA
<213> ORGANISM: Artificial Sequence
<220> FEATURE:
<223> OTHER INFORMATION: Primer

<400> SEQUENCE: 13
tttgctctgc ggccgcagag gccgtggggt cttcgctgtg gtgcg               45

<210> SEQ ID NO 14
<211> LENGTH: 46
<212> TYPE: DNA
<213> ORGANISM: Artificial Sequence
<220> FEATURE:
<223> OTHER INFORMATION: Primer

<400> SEQUENCE: 14
tttgctctgc ggccgcagag gccgattgtg gttttggtgt cttggg              46

<210> SEQ ID NO 15
<211> LENGTH: 13
<212> TYPE: DNA
<213> ORGANISM: Artificial Sequence
<220> FEATURE:
<223> OTHER INFORMATION: SfiI(a) site

<400> SEQUENCE: 15
ggcccagccg gcc                                                  13

<210> SEQ ID NO 16
<211> LENGTH: 13
<212> TYPE: DNA
<213> ORGANISM: Artificial Sequence
<220> FEATURE:
<223> OTHER INFORMATION: SfiI(b) site

<400> SEQUENCE: 16
ggcctctgcg gcc                                                  13
```

<210> SEQ ID NO 17
<211> LENGTH: 4057
<212> TYPE: DNA
<213> ORGANISM: Artificial Sequence
<220> FEATURE:
<223> OTHER INFORMATION: Plasmid Vector 1

<400> SEQUENCE: 17

| | | | | | | |
|---|---|---|---|---|---|---|
| gacgaaaggg | cctcgtgata | cgcctatttt | tataggttaa | tgtcatgata | ataatggttt | 60 |
| cttagacgtc | aggtggcact | tttcggggaa | atgtgcgcgg | aaccccctatt | tgtttatttt | 120 |
| tctaaataca | ttcaaatatg | tatccgctca | tgagacaata | accctgataa | atgcttcaat | 180 |
| aatattgaaa | aaggaagagt | atgagtattc | aacatttccg | tgtcgccctt | attccctttt | 240 |
| ttgcggcatt | ttgccttcct | gttttgctc | acccagaaac | gctggtgaaa | gtaaaagatg | 300 |
| ctgaagatca | gttgggtgca | cgagtgggtt | acatcgaact | ggatctcaac | agcggtaaga | 360 |
| tccttgagag | ttttcgcccc | gaagaacgtt | ttccaatgat | gagcactttt | aaagttctgc | 420 |
| tatgtggcgc | ggtattatcc | cgtattgacg | ccgggcaaga | gcaactcggt | cgccgcatac | 480 |
| actattctca | gaatgacttg | gttgagtact | caccagtcac | agaaaagcat | cttacggatg | 540 |
| gcatgacagt | aagagaatta | tgcagtgctg | ccataaccat | gagtgataac | actgcggcca | 600 |
| acttacttct | gacaacgatc | ggaggaccga | aggagctaac | cgcttttttg | cacaacatgg | 660 |
| gggatcatgt | aactcgcctt | gatcgttggg | aaccggagct | gaatgaagcc | ataccaaacg | 720 |
| acgagcgtga | caccacgatg | cctgtagcaa | tggcaacaac | gttgcgcaaa | ctattaactg | 780 |
| gcgaactact | tactctagct | tcccggcaac | aattaataga | ctggatggag | gcggataaag | 840 |
| ttgcaggacc | acttctgcgc | tcggcccttc | cggctggctg | gtttattgct | gataaatctg | 900 |
| gagccggtga | gcgtgggtct | cgcggtatca | ttgcagcact | ggggccagat | ggtaagccct | 960 |
| cccgtatcgt | agttatctac | acgacgggga | gtcaggcaac | tatggatgaa | cgaaatagac | 1020 |
| agatcgctga | gataggtgcc | tcactgatta | agcattggta | actgtcagac | caagtttact | 1080 |
| catatatact | ttagattgat | ttaaaacttc | atttttaatt | taaaaggatc | taggtgaaga | 1140 |
| tcctttttga | taatctcatg | accaaaatcc | cttaacgtga | gttttcgttc | cactgagcgt | 1200 |
| cagaccccgt | agaaaagatc | aaaggatctt | cttgagatcc | ttttttttctg | cgcgtaatct | 1260 |
| gctgcttgca | aacaaaaaaa | ccaccgctac | cagcggtggt | ttgtttgccg | gatcaagagc | 1320 |
| taccaactct | ttttccgaag | gtaactggct | tcagcagagc | gcagatacca | aatactgtcc | 1380 |
| ttctagtgta | gccgtagtta | ggccaccact | tcaagaactc | tgtagcaccg | cctacatacc | 1440 |
| tcgctctgct | aatcctgtta | ccagtggctg | ctgccagtgg | cgataagtcg | tgtcttaccg | 1500 |
| ggttggactc | aagacgatag | ttaccggata | aggcgcagcg | gtcgggctga | acggggggtt | 1560 |
| cgtgcacaca | gcccagcttg | gagcgaacga | cctacaccga | actgagatac | ctacagcgtg | 1620 |
| agctatgaga | aagcgccacg | cttcccgaag | ggagaaaggc | ggacaggtat | ccggtaagcg | 1680 |
| gcagggtcgg | aacaggagag | cgcacgaggg | agcttccagg | gggaaacgcc | tggtatcttt | 1740 |
| atagtcctgt | cgggtttcgc | cacctctgac | ttgagcgtcg | attttgtga | tgctcgtcag | 1800 |
| gggggcggag | cctatggaaa | aacgccagca | acgcggcctt | tttacggttc | ctggccttt | 1860 |
| gctggccttt | tgctcacatg | ttctttcctg | cgttatcccc | tgattctgtg | gataaccgta | 1920 |
| ttaccgcctt | tgagtgagct | gataccgctc | gccgcagccg | aacgaccgag | cgcagcgagt | 1980 |
| cagtgagcga | ggaagcggaa | gagcgcccaa | tacgcaaacc | gcctctcccc | gcgcgttggc | 2040 |

```
cgattcatta atgcagctgg cacgacaggt ttcccgactg aaagcgggc  agtgagcgca      2100 acgcaattaa tgtgagttag ctcactcatt aggcacccca ggctttacac tttatgcttc      2160
cggctcgtat gttgtgtgga attgtgagcg ataacaatt  tcacacagga acagctatg       2220 accatgatta cgccaagctt cgaaggagac agtcataatg aaatacctgc tgccgaccgc      2280
tgctgctggt ctgctgctcc tcgcggccca gccggccatg gagctcaaga tgacacagac      2340
tacatcctcc ctgtcagcct ctctgggaga cagagtcacc atcagttgca gggcaagtca      2400
ggacattagc gattatttaa actggtatca gcagaaacca gatggaactg ttaaactcct      2460
gatctattac acatcaagtt acactcagg  agtcccatca aggttcagtg gcggtgggtc       2520
tggaacagat tattctctca ccattagcaa cctggagcaa aagatattg  ccacttactt       2580 ttgccaacag ggtaatacgc ttccgtggac gtttggtgga ggcaccaagc tggaaatcaa      2640
acgggctgat gctgcaccaa ctgtaggcct ctgcggccgc agagcaaaaa ctcatctcag      2700
aagaggatct gaatgggccc gcatagggtt ccggtgattt tgattatgaa aagatggcaa      2760
acgctaataa gggggctatg accgaaaatg ccgatgaaaa cgcgctacag tctgacgcta      2820
aaggcaaact tgattctgtc gctactgatt acggtgctgc tatcgatggt tcattggtg       2880 acgtttccgg ccttgctaat ggtaatggtg ctactggtga ttttgctggc tctaattccc      2940
aaatggctca gtcggtgac  ggtgataatt cacctttaat gaataatttc cgtcaatatt       3000
taccttccct ccctcaatcg gttgaatgtc gccctttttgt ctttagcgct ggtaaaccat     3060
atgaattttc tattgattgt gacaaaataa acttattccg tggtgtcttt gcgtttcttt      3120
tatatgttgc cacctttatg tatgtatttt ctacgtttgc taacatactg cgtaataagg      3180
agtcttaata agaattcact ggccgtcgtt ttacaacgtc gtgactggga aaaccctggc      3240
gttacccaac ttaatcgcct tgcagcacat ccccctttcg ccagctggcg taatagcgaa      3300
gaggcccgca ccgatcgccc ttcccaacag ttgcgcagcc tgaatggcga atggcgcctg      3360
atgcggtatt ttctccttac gcatctgtgc ggtatttcac accgcatatg aaaattgtaa      3420
gcgttaatat tttgttaaaa ttcgcgttaa attttttgtta aatcagctca ttttttaacc    3480
aataggccga atcggcaaa  atcccttata aatcaaaaga atagaccgag atagggttga      3540
gtgttgttcc agtttggaac aagagtccac tattaaagaa cgtggactcc aacgtcaaag      3600
ggcgaaaaac cgtctatcag ggcgatggcc cactacgtga accatcaccc taatcaagtt      3660
ttttggggtc gaggtgccgt aaagcactaa atcggaaccc taaagggagc cccgattta       3720 gagcttgacg gggaaagccg gcgaacgtgg cgagaaagga agggaagaaa gcgaaggag       3780 cgggcgctag ggcgctggca agtgtagcgg tcacgctgcg cgtaaccacc acacccgccg      3840
cgcttaatgc gccgctacag ggcgcgtccc atatggtgca ctctcagtac aatctgctct      3900
gatgccgcat agttaagcca gccccgacac ccgccaacac ccgctgacgc gccctgacgg      3960
gcttgtctgc tcccggcatc cgcttacaga caagctgtga ccgtctccgg gagctgcatg      4020
tgtcagaggt tttcaccgtc atcaccgaaa cgcgcga                               4057
```

<210> SEQ ID NO 18
<211> LENGTH: 342
<212> TYPE: DNA
<213> ORGANISM: Artificial Sequence
<220> FEATURE:
<223> OTHER INFORMATION: DNA coding for anti-NP VHH antibody

<400> SEQUENCE: 18

```
cagttgcagc tcgtggagtc tgggggaggc ttggtgcagg ctggggggtc tctgagactc       60
```

```
tcctgtgcag cctctggaag cgccttcagc ctctatgcca tgggctggca ccgccaggct    120
ccagggaagc agcgcgagtt ggtcgcatat attactaatg gtgacatcac aaactatgcg    180
gactccgtgc agggccgtgt catcatctcc agagacaacg ccaaaaacac ggtgtatcta    240
cacatgaaca gcctgaaacc tgaggacaca gccgtctatt attgttatgc agtgggggt     300 cggaccttct ggggccaggg gacccaggtc accgtctcct ca                       342
```

<210> SEQ ID NO 19
<211> LENGTH: 39
<212> TYPE: DNA
<213> ORGANISM: Artificial Sequence
<220> FEATURE:
<223> OTHER INFORMATION: Primer

<400> SEQUENCE: 19

```
cagccggcca tggctcagtt gcagctcgtg gagtctggg                            39
```

<210> SEQ ID NO 20
<211> LENGTH: 38
<212> TYPE: DNA
<213> ORGANISM: Artificial Sequence
<220> FEATURE:
<223> OTHER INFORMATION: Primer

<400> SEQUENCE: 20

```
atggtgtgcg gccgctgagg agacggtgac ctgggtcc                             38
```

<210> SEQ ID NO 21
<211> LENGTH: 372
<212> TYPE: DNA
<213> ORGANISM: Artificial Sequence
<220> FEATURE:
<223> OTHER INFORMATION: DNA including the gene sequence coding for the
      amino acid sequence represented by SEQ ID NO: 8

<400> SEQUENCE: 21

```
cagccggcca tggctcagtt gcagctcgtg gagtctgggg gaggcttggt gcaggctggg    60
gggtctctga gactcctctg tgcagcctct ggaagcgcct tcagcctcta tgccatgggc    120
tggcaccgcc aggctccagg gaagcagcgc gagttggtcg catatattac taatggtgac    180
atcacaaact atgcggactc cgtgcagggc cgtgtcatca tctccagaga caacgccaaa    240
aacacggtgt atctacacat gaacagcctg aaacctgagg acacagccgt ctattattgt    300
tatgcagtgg ggggtcggac cttctggggc caggggaccc aggtcaccgt ctcctcagcg    360
gccgcacacc at                                                       372
```

<210> SEQ ID NO 22
<211> LENGTH: 33
<212> TYPE: DNA
<213> ORGANISM: Artificial Sequence
<220> FEATURE:
<223> OTHER INFORMATION: Primer

<400> SEQUENCE: 22

```
gcggccgcac accatcatca ccaccattaa tag                                  33
```

<210> SEQ ID NO 23
<211> LENGTH: 31
<212> TYPE: DNA
<213> ORGANISM: Artificial Sequence
<220> FEATURE:
<223> OTHER INFORMATION: Primer

<400> SEQUENCE: 23
agccatggcc ggctgggccg cgagtaataa c                                    31

<210> SEQ ID NO 24
<211> LENGTH: 498
<212> TYPE: PRT
<213> ORGANISM: Artificial Sequence
<220> FEATURE:
<223> OTHER INFORMATION: Recombinant nuclear protein

<400> SEQUENCE: 24

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
```

```
                340             345             350
Leu Pro Arg Gly Lys Leu Ser Thr Arg Gly Val Gln Ile Ala Ser Asn
            355                 360                 365
Glu Asn Met Glu Thr Met Glu Ser Ser Thr Leu Glu Leu Arg Ser Arg
        370                 375                 380
Tyr Trp Ala Ile Arg Thr Arg Ser Gly Gly Asn Thr Asn Gln Gln Arg
385                 390                 395                 400
Ala Ser Ala Gly Gln Ile Ser Ile Gln Pro Thr Phe Ser Val Gln Arg
                405                 410                 415
Asn Leu Pro Phe Asp Arg Thr Thr Ile Met Ala Ala Phe Asn Gly Asn
            420                 425                 430
Thr Glu Gly Arg Thr Ser Asp Met Arg Thr Glu Ile Ile Arg Met Met
        435                 440                 445
Glu Ser Ala Arg Pro Glu Asp Val Ser Phe Gln Gly Arg Gly Val Phe
    450                 455                 460
Glu Leu Ser Asp Glu Lys Ala Ala Ser Pro Ile Val Pro Ser Phe Asp
465                 470                 475                 480
Met Ser Asn Glu Gly Ser Tyr Phe Phe Gly Asp Asn Ala Glu Glu Tyr
                485                 490                 495
Asp Asn
```

<210> SEQ ID NO 25
<211> LENGTH: 3096
<212> TYPE: DNA
<213> ORGANISM: Artificial Sequence
<220> FEATURE:
<223> OTHER INFORMATION: DNA amplified from Vector pRA2

<400> SEQUENCE: 25

```
gcggccgcac accatcatca ccaccattaa tagcactagt caagaggatc cggctgctaa     60
caaagcccga aggaagctg  agttggctgc tgccaccgct gagcaataac tagcataacc    120
ccttggggcc tctaaacggg tcttgagggg ttttttgctg aaaggaggaa ctatatccgg    180
atgaattccg tgtattctat agtgtcacct aaatcgtatg tgtatgatac ataaggttat    240
gtattaattg tagccgcgtt ctaacgacaa tatgtacaag cctaattgtg tagcatctgg    300
cttactgaag cagaccctat catctctctc gtaaactgcc gtcagagtcg gtttggttgg    360
acgaaccttc tgagtttctg gtaacgccgt cccgcacccg gaaatggtca gcgaaccaat    420
cagcagggtc atcgctagcc agatcctcta cgccggacgc atcgtggccg gcatcaccgg    480
cgccacaggt gcggttgctg gcgcctatat cgccgacatc accgatgggg aagatcgggc    540
tcgccacttc gggctcatga gcgcttgttt cggcgtgggt atggtggcag gccccgtggc    600
cggggggactt ttgggcgcca tctccttgca tgcaccattc cttgcggcgg cggtgctcaa    660
cggcctcaac ctactactgg gctgcttcct aatgcaggag tcgcataagg gagagcgtcg    720
aatggtgcac tctcagtaca atctgctctg atgccgcata gttaagccag ccccgacacc    780
cgccaacacc cgctgacgcg ccctgacggg cttgtctgct cccggcatcc gcttacagac    840
aagctgtgac cgtctccggg agctgcatgt gtcagaggtt ttcaccgtca tcaccgaaac    900
gcgcgagacg aaagggcctc gtgatacgcc tatttttata ggttaatgtc atgataataa    960
tggtttctta gacgtcaggt ggcacttttc ggggaaatgt gcgcggaacc cctatttgtt   1020
tatttttcta aatacattca aatatgtatc cgctcatgag acaataaccc tgataaatgc   1080
ttcaataata ttgaaaaagg aagagtatga gtattcaaca tttccgtgtc gcccttattc   1140
```

```
ccttttttgc ggcatttttgc cttcctgttt ttgctcaccc agaaacgctg gtgaaagtaa    1200
aagatgctga agatcagttg ggtgcacgag tgggttacat cgaactggat ctcaacagcg    1260
gtaagatcct tgagagtttt cgccccgaag aacgttttcc aatgatgagc acttttaaag    1320
ttctgctatg tggcgcggta ttatcccgta ttgacgccgg gcaagagcaa ctcggtcgcc    1380
gcatacacta ttctcagaat gacttggttg agtactcacc agtcacagaa aagcatctta    1440
cggatggcat gacagtaaga gaattatgca gtgctgccat aaccatgagt gataacactg    1500
cggccaactt acttctgaca acgatcggag gaccgaagga gctaaccgct tttttgcaca    1560
acatggggga tcatgtaact cgccttgatc gttgggaacc ggagctgaat gaagccatac    1620
caaacgacga gcgtgacacc acgatgcctg tagcaatggc aacaacgttg cgcaaactat    1680
taactggcga actacttact ctagcttccc ggcaacaatt aatagactgg atggaggcgg    1740
ataaagttgc aggaccactt ctgcgctcgg cccttccggc tggctggttt attgctgata    1800
aatctggagc cggtgagcgt gggtctcgcg gtatcattgc agcactgggg ccagatggta    1860
agccctcccg tatcgtagtt atctacacga cggggagtca ggcaactatg gatgaacgaa    1920
atagacagat cgctgagata ggtgcctcac tgattaagca ttggtaactg tcagaccaag    1980
tttactcata tactttag attgatttaa aacttcattt ttaatttaaa aggatctagg    2040
tgaagatcct ttttgataat ctcatgacca aaatccctta acgtgagttt tcgttccact    2100
gagcgtcaga ccccgtagaa aagatcaaag gatcttcttg agatcctttt tttctgcgcg    2160
taatctgctg cttgcaaaca aaaaaaccac cgctaccagc ggtggtttgt ttgccggatc    2220
aagagctacc aactcttttt ccgaaggtaa ctggcttcag cagagcgcag ataccaaata    2280
ctgttcttct agtgtagccg tagttaggcc accacttcaa gaactctgta gcaccgccta    2340
catacctcgc tctgctaatc ctgttaccag tggctgctgc cagtggcgat aagtcgtgtc    2400
ttaccgggtt ggactcaaga cgatagttac cggataaggc gcagcggtcg ggctgaacgg    2460
ggggttcgtg cacacagccc agcttggagc gaacgaccta caccgaactg agatacctac    2520
agcgtgagct atgagaaagc gccacgcttc ccgaagggag aaaggcggac aggtatccgg    2580
taagcggcag ggtcggaaca ggagagcgca cgagggagct tccaggggga aacgcctggt    2640
atctttatag tcctgtcggg tttcgccacc tctgacttga gcgtcgattt ttgtgatgct    2700
cgtcaggggg gcggagccta tggaaaaacg ccagcaacgc ggccttttta cggttcctgg    2760
ccttttgctg gccttttgct cacatgttct ttcctgcgtt atccctgat tctgtggata    2820
accgtattac cgcctttgag tgagctgata ccgctcgccg cagccgaacg accgagcgca    2880
gcgagtcagt gagcgaggaa gcggaagagc gcccaatacg caaaccgcct ctccccgcgc    2940
gttggccgat tcattaatgc agctggctta tcgaaattaa tacgactcac tatagggaga    3000
cccaagcttt atttcaagga gacagtcata atgaaatacc tattgcctac ggcagccgct    3060
ggattgttat tactcgcggc ccagccggcc atggct                              3096
```